US010238606B2

(12) United States Patent
Fathi et al.

(10) Patent No.: US 10,238,606 B2
(45) Date of Patent: *Mar. 26, 2019

(54) PHARMACEUTICAL COMPOSITIONS FOR THE TREATMENT OF *HELICOBACTER PYLORI*

(71) Applicant: RedHill Biopharma Ltd., Tel-Aviv (IL)

(72) Inventors: Reza Fathi, Oradell, NJ (US); Gilead Raday, Palo Alto, CA (US); Guy Goldberg, Tel Aviv (IL); Patrick Gosselin, Laval (CA)

(73) Assignee: RedHill Biopharma Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/466,305

(22) Filed: Mar. 22, 2017

(65) Prior Publication Data

US 2017/0189341 A1 Jul. 6, 2017

Related U.S. Application Data

(63) Continuation of application No. 15/135,309, filed on Apr. 21, 2016, now Pat. No. 9,603,806, which is a continuation of application No. 14/522,921, filed on Oct. 24, 2014, now Pat. No. 9,498,445, which is a continuation of application No. 14/179,197, filed on Feb. 12, 2014, now Pat. No. 9,050,263.

(60) Provisional application No. 61/764,401, filed on Feb. 13, 2013, provisional application No. 61/764,385, filed on Feb. 13, 2013.

(51) Int. Cl.
*A61K 9/48* (2006.01)
*A61K 9/50* (2006.01)
*A61K 31/43* (2006.01)
*A61K 31/395* (2006.01)
*A61K 31/435* (2006.01)
*A61K 31/438* (2006.01)
*A61K 31/4439* (2006.01)

(52) U.S. Cl.
CPC .......... *A61K 9/4808* (2013.01); *A61K 9/4866* (2013.01); *A61K 9/4891* (2013.01); *A61K 9/5026* (2013.01); *A61K 9/5047* (2013.01); *A61K 9/5084* (2013.01); *A61K 31/395* (2013.01); *A61K 31/43* (2013.01); *A61K 31/435* (2013.01); *A61K 31/438* (2013.01); *A61K 31/4439* (2013.01)

(58) Field of Classification Search
CPC .. A61K 31/43; A61K 31/435; A61K 31/4439; A61K 9/4808; A61K 31/395; A61K 9/4891
See application file for complete search history.

(56) References Cited

U.S. PATENT DOCUMENTS 3,980,637 A * 9/1976 Grossman ............ C07D 499/68
540/317
4,738,974 A * 4/1988 Brandstrom ......... C07D 401/12
514/338
5,927,500 A * 7/1999 Godfrey ............. B65D 83/0463
206/461
6,489,317 B1 * 12/2002 Borody ................ A61K 33/245
424/653
9,050,263 B2 * 6/2015 Fathi .................... A61K 9/4891
9,498,445 B2 * 11/2016 Fathi .................... A61K 9/4891
9,603,806 B2 * 3/2017 Fathi .................... A61K 9/4891
2009/0028941 A1 1/2009 Cowles et al.
2009/0220611 A1 9/2009 Dargelas et al.
2014/0227353 A1 8/2014 Fathi et al.

FOREIGN PATENT DOCUMENTS

| CN | 101584681 A | 11/2009 |
|---|---|---|
| CN | 101607086 A | 12/2009 |
| CN | 101888828 A | 11/2010 |
| CN | 102091084 B | 5/2012 |
| EP | 1 803 450 A1 | 7/2007 |
| JP | 2000128779 A | 5/2000 |
| WO | 1996/024375 A1 | 8/1996 |
| WO | 2005/048979 A2 | 6/2005 |
| WO | 2009/017716 A2 | 2/2009 |
| WO | 2009138884 A2 | 11/2009 |

OTHER PUBLICATIONS

Bayerdorffer et al., "Double-Blind Trial of Omeprazole and Amoxicillin to Cure Helicobacter pylori Infection in Patients With Duodenal Ulcers", May 1995, Gastroenterology, vol. 108, No. 5, pp. 1412-1417. (Year: 1995).*
AGA (American Gastroenterological Association), "American Gastroenterological Association Medical Position Statement: Evaluation of Dyspepsia", Gastroenterology (2005), 129:1753-1755.
Akada, Junko K. et al., "In Vitro Anti-Helicobacter pylori Activities of New Rifamycin Derivatives, KRM-1648 and KRM-1657", Antimicrob Agents and Chemotherapy (1999), 43(5):1072 1076.
Dr. Reddys Laboratories Inc., Amoxicillin Capsules and Amoxicillin Powder, for Suspension, Package Insert (May 2012).
Apseloff, Glen M.D., "Severe neutropenia among healthy volunteers given rifabutin in clinical trials", Clinical Pharmacology and Therapeutics (Dec. 2003), 74:591-592.
Axon, A.T.R., "Campylobacter pylori-therapy review", Scand. J. Gastroenterol (1989), 24 Suppl. 160:35-38.
Axon, Anthony et al., "Helicobacter gastroduodenitis: a serious infectious disease", British Medical Journal. (1997), 314:1430-1431.
Barzilay, Ezra J., Chapter 3: Infectious Diseases Related to Travel, IN:2012 Yellow Book—Travelers' Health—CDC. (2011), New York: Oxford University Press Inc.

(Continued)

*Primary Examiner* — Michael B. Pallay
(74) *Attorney, Agent, or Firm* — Greenberg Traurig, LLP

(57) ABSTRACT

Single oral solid dosage form comprising an immediate release first dosage composition having at least two antibiotic agents and a delayed release second dosage composition having a proton pump inhibitor are provided herein. The single oral solid dosage form according to some aspects of the invention can be used for the treatment of disorders associated with infection by *H. pylori* or the prevention of recurrence of disorders associated with infection by *H. pylori*.

6 Claims, 6 Drawing Sheets

(56) References Cited

OTHER PUBLICATIONS

Bazzoli, Franco et al., "Short-term low-dose triple therapy for the eradication of Helicobacter pylori", Eur. J. Gastroenterol Hepatol. (1994), 6:773-777.
Beales, Ian LP., "Efficacy of Helicobacter pylori eradication therapies: a single centre observational study", BioMed Central, Gastroenterology (2001), 1:7.
Behrens, Rolf et al., "Dual versus triple therapy of Helicobacter pylori infection: results of a multicentre trial", Arch Dis Child (Jul. 1999), 81:68-70.
Bock, H. M.D. et al., "Rifabutin-based triple therapy after failure of Helicobacter pylori eradication treatment: preliminary experience", J. Clin. Gastroenterol. (2000), 31:222-225.
Borody, T.J et al., "Symptoms improve after the eradication of gastric Campylobacter pyloridis", Medical J. Australia. (1987), 146:450-451.
Borody, T.J. and Brandi S, Andrews P. et al., H. Pylori eradication failure (EF)—further treatment possibilities, Gastroenterology. (1992), 102:A43.
Borody, T.J. et al., "Efficacy and safety of rifabutin-containing 'rescue therapy' for resistant Helicobacter pylori infection", Aliment Pharmacology Therap. (2006) 23:481-488.
Brogden, Rex N. et al., "A review of its antimicrobial activity, pharmacokinetic properties and therapeutic efficacy", Drug Evaluation., Drugs (1994), 47:983-1009.
Broutet, N. et al. "Risk factors for failure of Helicobacter pylori therapy—results of an individual data analysis of 2751 patients", Aliment Pharmacol. Therap. (2003), 17:99-109.
Burman, William et al., "Acquired rifamycin resistance with twice-weekly treatment of HIV-related tuberculosis", Am. J. Respir. Crit. Care Med. (2006), 173:350-356.
Canducci, F. et al., "Rifabutin-based Helicobacter pylori eradication 'rescue therapy'", Aliment Pharmacol. Ther. (Jan. 2001), 15:143.
Cardenas, Victor M. et al., "Iron deficiency and Helicobacter pylori infection in the United States", Am. J. Epidemiology (2006), 163:127-134.
Cardenas, Victor M. et al., Helicobacter pylori Eradication and Its Effect on Iron Stores: A Reappraisal, J. Infect. Dis. (2006), 194:714.
Chey, William D. et al., "Noninvasive Helicobacter pylori testing for the "test-and-treat" strategy: A decision analysis to assess the effect of past infection on test choice", Arch. Intern. Med. (2001), 161:2129-2132.
Chey, William D. et al., "American College of Gastroenterology guideline on the management of Helicobacter pylori infection", Am. J. Gastroenterol. (2007), 102:1808-1825.
D'Elios, Mario M. et al., "Helicobacter pylori: usefulness of an empirical fourth-line rifabutin-based regimen", Expert Rev. Gastroenterol Hepatol. (2012), 6:437-439.
De Francesco, Vincenzo et al., Worldwide H. pylori Antibiotic Resistance: a Systematic Review, J. Gastrointestin. Liver Dis. (2010), 19:409-414.
Dholakia, K.R. et al., "Vitamin B12 deficiency and gastric histopathology in older patients", World J. Gastroenterol. (2005), 11(45):7078-7083.
DuBois, Suja et al., "Iron-deficiency anemia and Helicobacter pylori infection: a review of the evidence", Am. J. Gastroenterol. (2005), 100:453-459.
Duck, William M. et al., "Antimicrobial resistance incidence and risk factors among Helicobacter pylori infected persons, United States", Emerg. Infect. Dis. (2004), 10:1088-1094.
Ekstrom, Anna Mia et al., "Helicobacter pylori in gastric cancer established by CagA immunoblot as a marker of past infection", Gastroenterology. (2010), 121(4):784-791.
Fiorini, G. et al., "Culture-Based Selection Therapy for Patients Who Did Not Respond to Previous Treatment for Helicobacter pylori Infection", Clin. Gastroenterol. Hepatol. (Dec. 22, 2012), pii: S1542-3565(12)01507-8. doi: 10.1016/j.cgh.2012.12.007. [Epub ahead of print].
Ford, Alexander C. et al., "Epidemiology of Helicobacter pylori infection and Public Health Implications", Helicobacter. (2010), 15 (Suppl.1):1-6.
Gisbert, J.P. et al., "Review article: Helicobacter pylori 'rescue' regimen when proton pump inhibitor-based triple therapies fail", Aliment Pharmacol. Ther. (2002), 16:1047-1057.
Gisbert, J.P. et al., "Third-line rescue therapy with levofloxacin is more effective than rifabutin rescue regime after two Helicobacter pylori treatment failures", Aliment Pharmacol. Ther. (2006), 24:1469-1474.
Gisbert, J.P., "Rescue regimens after Helicobacter pylori treatment failure", World J. Gastroenterol. (2008), 14 (35):5385-5402.
Gisbert, J.P., "Rescue Therapy for Helicobacter pylori Infection 2012", Gastroenterol Res. Pract. (2012a), epub. 974594.
Gisbert, J.P. et al., "Fourth-line rescue therapy with rifabutin in patients with three Helicobacter pylori eradication failures", Aliment Pharmacol. Ther. (2012c), 35(8):941-947.
Glocker, Erik et al., "Characterization of rifampicin-resistant clinical Helicobacter pylori isolates from Germany", Journal of Antimicrobial Chemotherapy. (2007), 59:874-879.
Glupczynski, Y. et al., "Lack of antibiotic compliance in patients treated for Campylobacter pylori-associated gastritis", Am. J. Gastroenterol. (1989), 84:1125-1126.
Goddard, Andrew F. et al., "Effect of omeprazole on the distribution of metronidazole, amoxicillin, and clarithromycin in human gastric juice", Gastroenterology. (1996), 111:358-367.
Godoy, Anita Paula Ortiz et al., "Analysis of antimicrobial susceptibility and virulence factors in Helicobacter pylori clinical isolates", BioMed Central, Gastroenterol. (2003), 11:3-20.
Gonzalez, Pedro Carro et al., "Efficacy of rifabutin-based triple therapy in Helicobacter pylori infected patients after two standard treatments", J. Gastroenterol. Hepatol. (2007), 22,60-63.
Graham, David Y. et al., "Seroepidemiology of Helicobacter pylori infection in India, Comparison of developing and developed countries", Dig. Dis. Sciences. (1991), 36:1084-1088.
Graham, Kathleen S. et al., "Variability with omeprazole-amoxicillin combinations for treatment of Helicobacter pylori infection", Am. J. Gastroenterol. (1995), 90:1415-1418.
Graham, David Y., "Editorial: Can therapy ever be denied for Helicobacter pylori infection?", Gastroenterology. (1997a), 113:S113-S117.
Graham, David Y., "Helicobacter pylori infection in the pathogenesis of duodenal ulcer and gastric cancer: a model", Gastroenterology. (1997b), 113:1983-1991.
Graham, David Y., "Efficient identification and evaluation of effective Helicobacter pylori therapies", Clin. Gastroenterol Hepatol. (2009), 7:145-148.
Graham, David Y. et al., "Clinical practice: diagnosis and evaluation of dyspepsia", J. Clin. Gastroenterol. (2010a), 44:167-172.
Graham, David Y., "Helicobacter pylori eradication therapy research: ethical issues and description of results", Clin. Gastroenterol Hepatol. (2010b), 8:1032-1036.
Graham, David Y. et al., "Helicobacter pylori therapy demystified", Helicobacter. (2011),16:343-345.
Graham, David Y. et al., "Guide regarding choice of second-line therapy to obtain a high cumulative cure rate", Helicobacter. (2012), 17:243-245.
Grayson, M.L. et al., "Effect of varying pH on the susceptibility of Campylobacter pylori to antimicrobial agents", Eur. J. Clin. Microbiol. Infect. Dis. (1989), 8:888-889.
Thyagarajan, S.P., et al., "Geographical difference in antimicrobial resistance pattern of Helicobacter pylori clinical isolates from Indian patients: Multicentric study", J. Gastroenterol. Hepatol. (2003), 18:1373-1378.
Toracchio, S. et al., "Rifabutin based triple therapy for eradication of H. pylori primary and secondary resistant to tinidazole and clarithromycin", Dig. Liver. Dis. (2005), 37:33-38.
Tseng, Alice L. et al., "Rifabutin-associated uveitis", Ann. Pharmacother. (1995), 29:1149-1155.
Tsuchiya, Mamiko et al., "Helicobacter pylori urease inhibition by rabeprazole, a proton pump inhibitor", Biol. Pharm. Bull. (Aug. 1995), 18 (8):1053-1056.

(56) References Cited

OTHER PUBLICATIONS

Unge, P. et al., "Does omeprazole improve antimicrobial therapy directed towards gastric Campylobacter pylori in patients with antral gastritis?", A pilot study. Scand. J. Gastroenterol. Suppl. (1989), 167:49-54.
Van Der, Poorten D. et al. "The effectiveness of rifabutin triple therapy for patients with difficult to eradicate Helicobacter pylori in clinical practice", Aliment Pharmacol. Ther. (2007), 26:1537-1542.
Walsh, John H. et al., "The treatment of Helicobacter pylori infection in the management of peptic ulcer disease", New Eng. J. Med. (1995), 333:984-991.
Wannmacher, Lennita, "Review of the evidence for H. pylori treatment regimens", Section 17.1 (Review)—Adults and Children. 18th Expert Committee on the Selection and Use of Essential Medicines. (2011), World Health Organization.
World Health Organization, "Treatment of Tuberculosis Guidelines", 4th edition (2010), 85.
Wong, B. C. Y. et al., "Comparison of lansoprazole-based triple and dual therapy for treatment of Helicobacter pylori-related duodenal ulcer: an Asian multicentre double-blind randomized placebo controlled study", Aliment Pharmacol. Ther. (2000), 14:217 224.
Wong, W. M. et al., "Randomized controlled study of rabeprazole, levofloxacin and rifabutin triple therapy vs. quadruple therapy as second-line treatment for Helicobacter pylori infection", Aliment. Pharmacol. Ther. (2003), 17:553-560.
PCT International Search Report and the Written Opinion of the International Searching Authority dated May 16, 2014 (11 pages).
Blaschke, Terrence F. et al., "The Clinical Pharmacokinetics of Rifabutin", Clinical Infectious Diseases, 1996: 22 (Suppl. 1):S15-22.
Gisbert, J. P. et al., "Review Article: Rifabutin in the Treatment of Refractory Helicobacter Pylori Infection", Aliment Pharmacal. Ther. 2012, www.medscape.com, 35(2), p. 209-221.
Dubois, Andre et al., "Transient and Persistent Experimental Infection of Nonhuman Primates with Helicobacter Pylori: Implications for Human Disease", Infection and Immunity, Aug. 1996, p. 2885-2891.
Robinson, M., "Review article: the pharmacodynamics and pharmacokinetics of proton pump inhibitors—overview and clinical implications", Aliment Pharmacal. Ther. 2004, 20 (Suppl. 6), p. 1-10.
Mainz, Dagmar et al., "Pharmacokinetics of lansoprazole, amoxicillin and clarithromycin after simultaneous and single administration", Journal of Antimicrobial Chemotherapy 2002, 50, p. 699-706.
Goddard, Andrew F. et al., "In Vitro Assessment of Gastric Mucosal Transfer of Anti-Helicobacter Therapeutic Agents", Antimicrobial Agents and Chemotherapy, Jun. 1997, p. 1246-1249.
Lozniewski A. et al., "Gastric diffusion of antibiotics used against Helicobacter pylori", International Journal of Antimicrobial Agents, 1998, p. 181-193.
Krishna, G. et al., "Evaluation of the pharmacokinetics of posaconazole and rifabutin following co-administration to healthy men", Current Medical Research and Opinion 2007, vol. 23 No. 3, p. 545-552.
Borody, T. J. et al., "Efficacy and saftey of rifabutin-containing 'rescue therapy' for resistant Helicobacter pylori infection", Alimentary Pharmacology & Therapeutics 2005, p. 481-488.
Abbreviated Drug Class Review: Proton Pump Inhibitors, VHA Pharmacy Benefits Management Strategic Healthcare Group and the Medical Advisory Panel, Aug. 2006.
Omerprazole Delayed-Release Capsules; Official Monographs/ Omeprazole, USP 35, pp. 4113-4115; 2014 U.S. Pharmacopeia National Formulary, Official Dec. 1, 2014 to Apr. 30, 2015.
Extended European Search Report from European Patent Application No. 14751025.9 dated Sep. 13, 2016.
Harford, William et al. "Double-blind, multicenter evaluation of lansoprazole and amoxicillin dual therapy for the cure of Helicobacter pylori infection", Helicobacter (1996), 1:243-250.
Heep, Markus et al., "Rifampin and rifabutin resistance mechanism in Helicobacter pylori", Antimicrobial Agents and Chemother. (1999), 43:1497-1499.
Kelleher, P. et al., "Uveitis associated with rifabutin and macrolide therapy for Mycobacterium avium intracellulare infection in AIDS patients", Genitourin Med. (1996), 72:419-421.
Kim, Jung Mogg et al., "Comparison of primary and secondary antimicrobial minimum inhibitory concentrations for Helicobacter pylori isolated from Korean patients", Int. J. Antimicrob Agents. (2006), 28:6-13.
Kim, Seung Young et al., "Effectiveness of three times daily lansoprazole/amoxicillin dual therapy for Helicobacter pylori infection in Korea", Br. J. Clin. Pharmacol. (2011), 73:1:140 143.
Kita, Tomoko et al., "CYP2C19 genotype related effect of omeprazole on intragastric pH and antimicrobial stability", Pharm. Res. (2001), 18:615-21.
Kumala, Widyasari et al., "Patterns of Helicobacter pylori isolate resistance to fluoroquinolones, amoxicillin, clarithromycin and metronidazole", Southeast Asian J. Trop Med Public Health. (2006), 37:970-974.
Kunin, Calvin M., "Antimicrobial activity of rifabutin", Clin. Infect. Dis. (1996), 2 (Suppl 1) S3-14.
Lee, Yi-Chia et al., "The benefit of mass eradication of Helicobacter pylori infection: a community-based study of gastric cancer prevention", Gut. (2013), 62(5):676-82, doi:10.1136/gutjnl-2012-302240, Epub. (Jun. 14, 2012).
Li, Albert P. et al., "Primary human hepatocytes as a tool for the evaluation of structure-activity relationship in cytochrome P450 induction potential of xenobiotics: evaluation of rifampin, rifapentine, and rifabutin", Chemico-Biological Interactions (1997), 107:17-30.
Li, Jiehui et al., "Relapse and acquired rifampin resistance in HIV infected patients with tuberculosis treated with rifampin- or rifabutin-based regimens in New York City, 1997-2000", Clin. Infect. Dis. (2005), 41:83-91.
Luther, Jay et al., "Empiric quadruple vs. triple therapy for primary treatment of Helicobacter pylori infection: systematic review and meta-analysis of efficacy and tolerability", Am. J. Gastroenterol. (2010), 105:65-73.
Maconi, Giovanni et al., "Predictors of long-term outcome of functional dyspepsia and duodenal ulcer after successful Helicobacter pylori eradication—a 7-year follow-up study", European. J. Gastroenterol Hepatol. (2009), 21(4):387-393.
Malfertheiner, P. et al., "Current European concepts in the management of helicobacter pylori infection—the Maastricht consensus report", The European Helicobacter pylori study group (EHPSG) Eur. J. Gastroenterol Hepatol. (1997), 9:1 2.
Malfertheiner, P., Management of H. pylori infection: Maastricht III—2005.
Malfertheiner, Peter et al., "Guidelines for the Management of Helicobacter pylori Infection", Business Review: European Gastroenterology Review (2005), 59-60, 998-999.
Malfertheiner, P. et al., "Helicobacter pylori eradication with a capsule containing bismuth subcitrate potassium, metronidazole, and tetracycline given with omeprazole versus clarithromycin-based triple therapy: a randomised, open-label, non-inferiority, phase 3 trial", The Lancet. (2011), 377:905-913.
Malfertheiner, Peter et al., "Management of Helicobacter pylori infection—the Maastricht IV/Florence Consensus report", Gut. (2012), 61:646-664.
Marshall, Barry J. et al., "Prospective double-blind trial of duodenal ulcer relapse after eradication of Campylobacter pylori", The Lancet. (Dec. 1988), 24/31, 2 (8626-8627):1437-1342.
Marshall, B. J., "Treatment strategies for Helicobacter pylori infection", Gastroenterol Clin. North Am. (1993), 22:183-198.
McNulty, Cliodna A. M. et al., "Campylobacter pyloridis and associated gastritis: investigator blind, placebo controlled trial of bismuth salicylate and erythromycin ethylsuccinate", British Medical Journal (1986), 293:645-649.
Megraud, F., "H pylori antibiotic resistance: prevalence, importance, and advances in testing", Gut. (2004), 53:1374-1384.
Megraud, Francis et al., "Helicobacter pylori resistance to antibiotics in Europe and its relationship to antibiotic consumption", Gut. (2013), 62:34-42.
Miehlke, S. et al., "Randomized trial of rifabutin-based triple therapy and high-dose dual therapy for rescue treatment of Helicobacter

(56) References Cited

OTHER PUBLICATIONS pylori resistant to both metronidazole and clarithromycin", Aliment Pharmacol. Ther. (2006), 24:395 403.
Miehlke, Stephan et al., "One-week once-daily triple therapy with esomeprazole, moxifloxacin, and rifabutin for eradication of persistent Helicobacter pylori resistant to both metronidazole and clarithromycin", Helicobacter. (2008), 13:69-74.
Moayyedi, P. et al., "Eradication of Helicobacter pylori for non-ulcer dyspepsia (Review)", The Cochrane Database of Systematic Reviews. (2006), 2:1-40.
Mycobutin® (rifabutin) Capsules, Package Insert, (Jan. 2010), Pharmacia and Upjohn Company.
Navarro-Jarabo, Jose M. et al., "Efficacy of rifabutin-based triple therapy as second-line treatment to eradicate Helicobacter pylori infection", BioMed Central, Gastroenterol. (2007), 7:31.
NCI. Surveillance Epidemiology and End Results, SEER Stat Fact Sheet: Stomach, http://seer.cancer.gov/statfacts/html/stomach.html, Accessed Mar. 2013.
Oderda, G. et al., "Campylobacter pylori gastritis: long term results of treatment with amoxycillin", Arch. Dis. Child. (1989), 64:326-329.
Omeclamox-Pak™ (omeprazole, clarithromycin, amoxicillin) Kit, Package Insert, (Feb. 2012), Pernix Therapeutics.
Perri, A. et al., "Treatment of antibiotic-resistant Helicobacter pylori Infection", The New England Journal of Medicine (1998), 33:53.
Perri, F. et al., "Rifabutin-based 'rescue therapy' for Helicobacter pylori infected patients after failure of standard regimens", Aliment Pharmacol. Ther. (2000), 14:311 316.
Perri, Francesco et al., "Randomized study of two "rescue" therapies for Helicobacter pylori-infected patients after failure of standard triple therapies", Am. J. Gastroenterol. (2001), 96:58-62.
Perucca, E. et al., Comparative effects of rifabutin and rifampicin on hepatic microsomal enzyme activity in normal subjects, Eur. J. Clin. Pharmacol. (1988), 34:595 599.
Prevpac® (lansoprazole, amoxicillin and clarithromycin) Kit, Package Insert, (Oct. 2009), Takeda Pharmaceuticals America.
Prilosec® (omeprazole) Delayed-Release Capsules and Prilosec® (omeprazole magnesium) for Delayed-Release Oral Suspension, Package Insert, (May 2013), AstraZeneca.
Protonix® (pantoprazole sodium) Tablet, Delayed Release and Protonix® (pantoprazole sodium) Granule, Delayed Release, Package Insert, (Oct. 2012), Wyeth.
Qasim, Asghar et al., "Rifabutin- and furazolidone-based Helicobacter pylori eradication therapies after failure of standard first- and second-line eradication attempts in dyspepsia patients", Aliment Pharmacol. Ther. (2005), 21:91-96.
Reinach, Benedetta et al., "Comparative effects of rifabutin and rifampicin on cytochromes P450 and UDP-glucuronosyl-transferases expression in fresh and cryopreserved human hepatocytes", Chem. Biol. Interact. (1999), 121:37-48.
Rimbara, Emiko et al., "Optimal therapy for Helicobacter pylori infections", Nature Reviews Gastroenterology & Hepatology (2011), 8:79-88.
Ronchera, C. L. et al., "Pharmacokinetic interaction between high-dose methotrexate and amoxicillin", Ther. Drug Monit. (1993), 15:375-379.
Salazar, Cesar O. et al., "Greater than 95% success with 14-day bismuth quadruple anti-Helicobacter pylori therapy: a pilot study in US Hispanics", Helicobacter. (2012), 17:382-390.
Salcedo, Julio A. et al., "Treatment of Helicobacter pylori infection", Arch. Intern. Med. (1998), 158:842-851.
Schwartz, H. et al, "Triple versus dual therapy for eradicating Helicobacter pylori and preventing ulcer recurrence: a randomized, double-blind, multicenter study of lansoprazole, clarithromycin, and/or amoxicillin in different dosing regimens", Am. J. Gastroenterol. (1998), 93:584-590.
Selgrad, Michael et al., "Clinical Aspects of Gastric Cancer and Helicobacter pylori—Screening, Prevention, and Treatment", Helicobacter. (2010), 15 (Suppl. 1), 40-45.
Shafran, Stephen D. et al., "A comparison of two regimens for the treatment of *Mycobacterium avium* complex bacteremia in AIDS: rifabutin, ethambutol, and clarithromycin versus rifampin, ethambutol, clofazimine, and ciprofloxacin", Canadian HIV Trials Network Protocol 010 Study Group. N. Engl. J. Med. (1996), 8 335:377-383.
Shirai, Naohito et al., "Dual therapy with high doses of rabeprazole and amoxicillin versus triple therapy with rabeprazole, amoxicillin, and metronidazole as a rescue regimen for Helicobacter pylori infection after the standard triple therapy", Eur. J. Clin. Pharmacol. (2007), 63:743-749.
Suzuki, Shoji et al., "Past rifampicin dosing determines rifabutin resistance of Helicobacter pylori", Digestion. (2009), 79:1-4.
Talley, Nicholas J., "Guidelines for the management of dyspepsia", Am. J. Gastroenterol. (2005), 100:2324-2337.
Sierra et al., "Ideal treatment for Helicobacter pylori: A systematic review"; Revista de Gastroenterologia de Mexico, 2014; 79(1): 28-49.

* cited by examiner

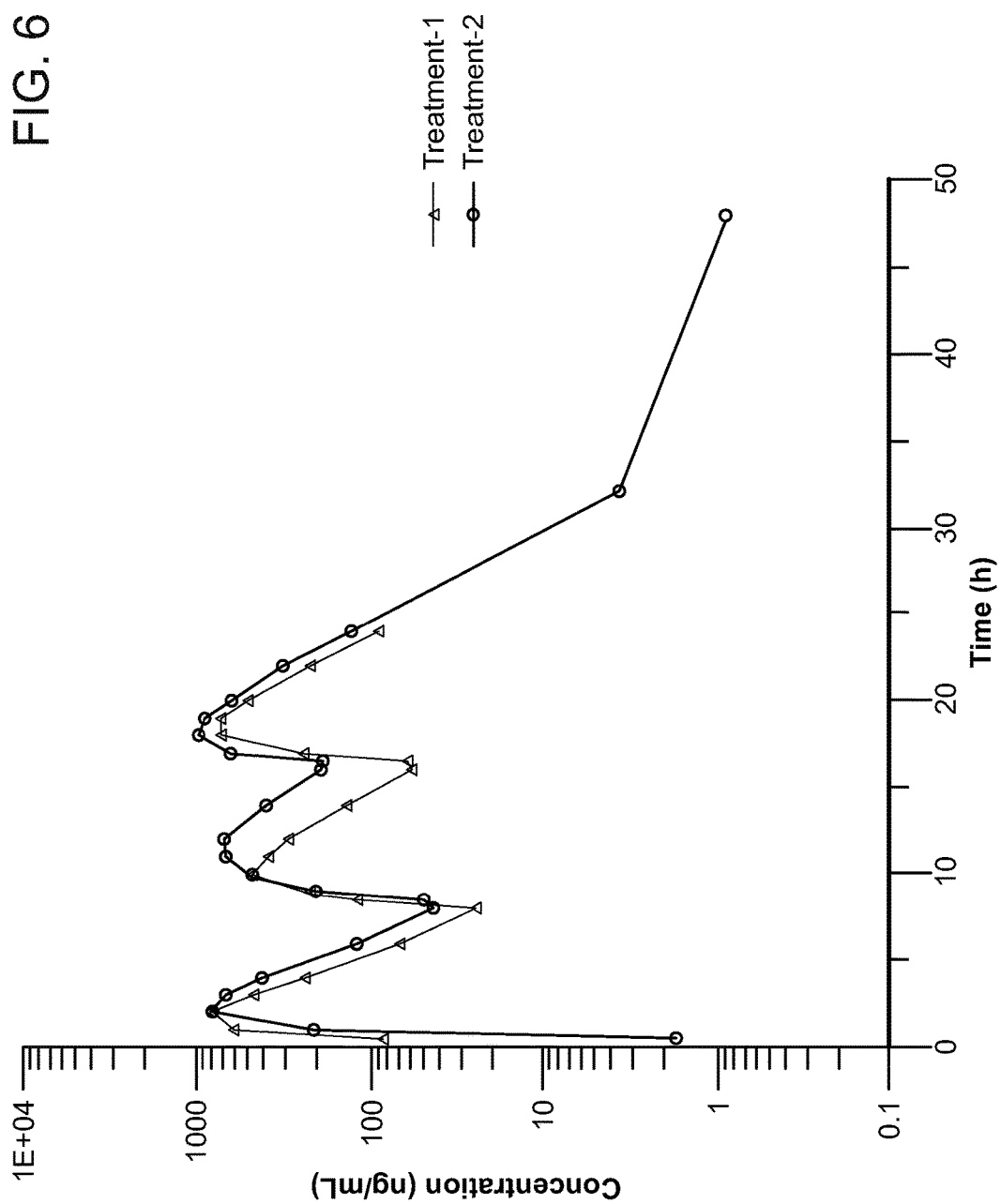

PHARMACEUTICAL COMPOSITIONS FOR THE TREATMENT OF *HELICOBACTER PYLORI*

CROSS-REFERENCE TO RELATED APPLICATIONS

This application is a continuation of U.S. patent application Ser. No. 15/135,309, filed Apr. 21, 2016, which is a continuation of U.S. patent application Ser. No. 14/522,921, filed Oct. 24, 2014, now U.S. Pat. No. 9,498,445, which is a continuation of U.S. patent application Ser. No. 14/179,197, filed Feb. 12, 2014, now U.S. Pat. No. 9,050,263, which claim the benefit of and priority to U.S. Provisional Application Ser. No. 61/764,385, filed Feb. 13, 2013, and U.S. provisional Application Ser. No. 61/764,401, filed Feb. 13, 2013, the entire disclosures of each of which are incorporated herein by reference in their entireties.

TECHNICAL FIELD

Aspects of the invention relate to compositions and methods for the treatment and/or prevention of recurrence of disorders associated with infection by *Helicobacter pylori* (*H. pylori*) and preparation methods thereof.

BACKGROUND

Historically, *Helicobacter pylori* (*H. pylori*) was found to be difficult to eradicate using known chemotherapeutic agents. Although many antibiotics can suppress *H. pylori* growth in vivo, the mucosal concentration appears to be inadequate and penetration of the usual gastric mucus layer is poor. Furthermore, there is frequently more than one infecting agent within the mucosa and hence, sensitivities of the various bacteria may vary within one patient and within one region of the mucosa. The development of adequate in vivo eradication methods for chronic *H. pylori* infection has therefore been difficult.

SUMMARY

Single oral solid dosage forms comprising a first immediate release dosage composition having at least two antibiotic agents and a delayed release second dosage composition having a proton pump inhibitor are provided herein. The single oral solid dosage form according to some aspects of the invention can be used for the treatment of disorders associated with infection by *H. pylori* or the prevention of recurrence of disorders associated with infection by *H. pylori*.

According to some aspects, the pharmaceutical composition comprises:

(1) an immediate release first dosage composition comprising at least two antibiotics;

(2) a delayed release second dosage composition comprising a proton pump inhibitor and a coating, wherein the coating is sufficiently designed to meet the two stage test dissolution profile in a basket apparatus:

(a) release of not more than 10% of the proton pump inhibitor in 120 min in an acid stage comprising 900 ml 0.1N HCl at 100 rpm; and (b) release of not less than 75% of the proton pump inhibitor in 45 min in 900 ml phosphate buffer pH 6.8 at 100 rpm following the acid stage; and (3) an outer layer encapsulating the first and the second dosage compositions.

In some embodiments, the coating in the second dosage composition can be designed to ensure that the release of the proton pump inhibitor is delayed from 120 to at least 240 minutes following oral administration.

In some embodiments, the first and second dosage compositions can be in the form of minitablets. In some embodiments, the pharmaceutical composition is in an oral solid dosage form. For example, the pharmaceutical composition can be in the form of a capsule, caplet, granules, powder, tablet, or pouch.

In some embodiments, the first dosage composition can comprise amoxicillin and ansamycin, derivatives thereof, or pharmaceutically acceptable salts and solvates thereof. Ansamycin can comprise rifampicin, rifabutin, derivatives thereof, pharmaceutically acceptable salts and solvates thereof or combinations thereof.

In some embodiments, in the second dosage composition, the proton pump inhibitor is one of omeprazole, pantoprazole, lansoprazole, ilaprazole, dexlansoprazole, esomeprazole and rabeprazole, pharmaceutically acceptable salt and solvates thereof or combinations thereof.

In some embodiments, the second dosage composition can comprise a time delay agent. The time delay agent can be one of sodium alginate, glyceryl monostearate, glyceryl distearate, forms of acrylic acids, forms of celluloses or combinations thereof.

In some embodiments, at least 70% of the at least two antibiotics can be released between 5 and 120 minutes following oral administration. In some embodiments, at least 70% of the proton inhibitor can be released between 120 and 240 min following oral administration.

In some embodiments, the pharmaceutical composition can comprise rifabutin, amoxicillin and omeprazole. According to some embodiments, the amoxicillin to rifabutin ratio can range from 10 to 40. According to some embodiments, the amoxicillin to omeprazole ratio can range from 20 to 40.

In some embodiments, the first and second dosage compositions can further comprise a filler, a disintegrant, a binder, a surfactant, an alkalizing agent, a lubricant or combinations thereof. The filler can be one of lactose, cellulose, starch, calcium phosphates, calcium carbonate, sugar, or combinations thereof. The disintegrant can be one of croscarmellose sodium, carboxymethyl cellulose, sodium starch glycolate, crospovidone or combinations thereof. The binder can be one of starch, cellulose, polyvinylpyrrolidone, xanthan gum, alginic acid, agar or combinations thereof. The surfactant can be one of sodium lauryl sulphate, polyoxyethylene polyoxypropylene glycol, polyethylene glycol, polypropylene glycol, polyvinyl caprolactam-polyvinyl acetate-polyethylene glycol, macrogolglycerol hydroxystearate or combinations thereof. The alkalizing agent can be one of meglumine, calcium carbonate, sodium sulfate, sodium bicarbonate or combinations thereof. The lubricant can be one of magnesium stearate, silicon dioxide, talc, stearic acid, sodium stearyl fumarate, glyceryl behenate or combinations thereof.

In some embodiments, the pharmaceutical composition can further comprise an outer coating. The coating can comprise a polymer, surfactant, plasticizer, opacifier, an alkalizing agent or combinations thereof.

According to some aspects of the invention, the pharmaceutical composition comprises an immediate release first dosage composition comprising 250 mg amoxicillin and 12.5 mg rifabutin, derivatives thereof, or pharmaceutically acceptable salts and solvates thereof and a delayed release second dosage composition comprising 10 mg omeprazole, derivatives thereof, or pharmaceutically acceptable salts and solvates thereof.

In some embodiments, the second dosage composition can comprise an outer protective layer, an enteric coating and an inner protective layer to protect the proton pump inhibitor from the enteric coating.

In some embodiments, the pharmaceutical composition is stable under standard room temperature and humidity conditions.

Some aspects of the invention relate to a method of treatment, the method comprising administering orally a dose of a pharmaceutical composition in a single solid dosage form, wherein the pharmaceutical composition comprises (1) an immediate release first dosage composition comprising at 12.5 mg rifabutin and 250 mg amoxicillin, derivatives thereof, or pharmaceutically acceptable salts and solvates thereof, (2) a delayed release second dosage composition comprising 10 mg omeprazole, derivatives thereof and pharmaceutically acceptable salts and solvates thereof and a coating, wherein the coating is sufficiently designed to meet the two stage test dissolution profile in a basket apparatus: (a) release of not more than 10% of omeprazole in 120 min in an acid stage comprising 900 ml 0.1N HCl at 100 rpm and (b) release of not less than 75% of omeprazole in 45 min in 900 ml phosphate buffer pH 6.8 at 100 rpm following the acid stage; and (3) an outer layer encapsulating the first and the second compositions, wherein in the step of administering, the dose comprises 50 mg rifabutin, 1000 mg amoxicillin, and 40 mg omeprazole and is administered three times per day.

In some embodiments, up to 3500 mg amoxicillin can be administered daily. In some embodiments, up to 4500 mg amoxicillin can be administered daily. In some embodiments, up to 300 mg rifabutin can be administered daily.

In some embodiments, the method can comprise treating a patient for at least 7 days, at least 10 days, at least 14 days. In some embodiments, the method of treating results in an eradication rate of $H.\ pylori$ greater than 80%, greater 85%, greater than 90%, greater than 95%. In some embodiments, treating a patient for at least 14 days results in an eradication rate of $H.\ pylori$ greater than 84%.

Aspects of the invention relate to a pharmaceutical composition and a method of treatment using the pharmaceutical composition. Such compositions and methods can be used to optimize the eradication effectiveness, the tolerability of the treatment and the dosing schedule in a patient.

Aspects of the invention relate to an effective drug therapy formulated to have optimal pharmacokinetic properties to deliver the active pharmaceutical ingredients.

In some aspects of the invention, the pharmaceutical composition, comprises: (1) an immediate release first dosage composition comprising a first antibiotic and at least a second antibiotic wherein the first antibiotic is rifabutin or derivatives thereof and pharmaceutically acceptable salts and solvates thereof, wherein the first dosage core comprises 12.5 mg rifabutin and provides, when administered at a dose of 50 mg three times a day to a human in a fasted state an in vivo plasma profile having (a) a mean $C_{max}$ of 87 ng/ml; (b) a Geometric LSMeans of 85 ng/ml; (c) a mean $AUC_{0-24}$ of 1320 ng·h/ml; and (c) a mean T max of 16.50 h based on a three times a day dose administration; (2) a delayed release second dosage composition comprising a proton pump inhibitor and a coating; and (3) an outer layer encapsulating the first dosage composition and the second dosage composition.

In some aspects of the invention, the pharmaceutical composition, comprises: (1) an immediate release first dosage composition comprising a first antibiotic and at least a second antibiotic wherein the first antibiotic is rifabutin or derivatives thereof and pharmaceutically acceptable salts and solvates thereof, wherein the first dosage core comprises 12.5 mg rifabutin and provides, when administered at a dose of 50 mg three times a day to a human in a fasted state an in vivo plasma profile having (a) a mean $C_{max}$ ranging from 60 ng/ml to 113 ng/ml; (b) a Geometric LSMeans ranging from 55 ng/ml to 110 ng/ml; (c) a mean $AUC_{0-24}$ ranging from 800 ng·h/ml to 1850 ng·h/ml; and (c) a mean T max ranging from 14 h to 19 h based on a three times a day dose administration; (2) a delayed release second dosage composition comprising a proton pump inhibitor and a coating; and (3) an outer layer encapsulating the first dosage composition and the second dosage composition.

In some aspects of the invention, the pharmaceutical composition, comprises: (1) an immediate release first dosage composition comprising a first antibiotic and at least a second antibiotic wherein the first antibiotic is rifabutin or derivatives thereof and pharmaceutically acceptable salts and solvates thereof, wherein the first dosage core comprises 12.5 mg rifabutin and provides, when administered at a dose of 50 mg three times a day to a human in a fasted state an in vivo plasma profile having (a) a $C_{max}$ to $C_{min}$ ratio of less than 57.8; and (b) a mean T max of 16.50 h based on a three times a day dose administration; (2) a delayed release second dosage composition comprising a proton pump inhibitor and a coating; and (3) an outer layer encapsulating the first dosage composition and the second dosage composition.

In some embodiments, the first dosage composition can comprise 250 mg amoxicillin and 12.5 mg rifabutin or derivatives thereof and pharmaceutically acceptable salts and solvates thereof and wherein the second dosage composition can comprise 10 mg omeprazole or derivatives thereof and pharmaceutically acceptable salts and solvates thereof.

In some embodiments, the pharmaceutical composition, comprises: (1) an immediate release first dosage composition comprising 250 mg amoxicillin and 12.5 mg rifabutin or derivatives thereof and pharmaceutically acceptable salts and solvates thereof, wherein the first dosage core comprises provides, when rifabutin is administered at a dose of 50 mg three times a day to a human in a fasted state an in vivo plasma profile having (a) a mean $C_{max}$ of 87 ng/ml; (b) a Geometric LSMeans of 85 ng/ml; (c) a mean $AUC_{0-24}$ of 1320 ng·h/ml (c) a mean T max of 16.50 h based on a three times a day dose administration; (2) a delayed release second dosage composition comprising a proton pump inhibitor and a coating; and (3) an outer layer encapsulating the first dosage composition and the second dosage composition.

BRIEF DESCRIPTION OF THE DRAWINGS

The presently disclosed embodiments will be further explained with reference to the drawings. The drawings are not necessarily in scale, with emphasis instead generally placed upon illustrating the principles of the presently disclosed embodiments.

Figure 2:
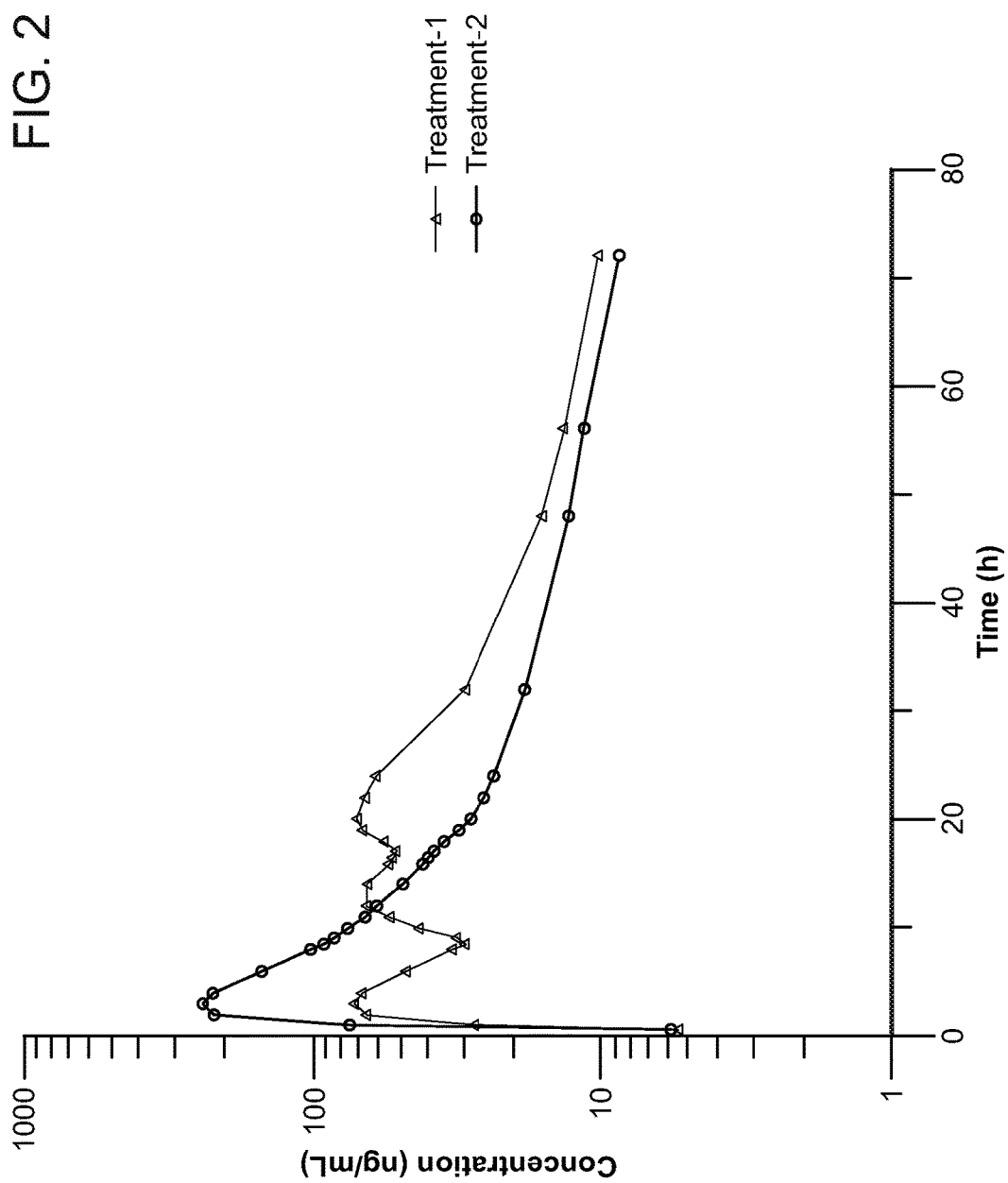

FIG. 2 illustrates the logarithmic profile of the mean for rifabutin in treatment 1 using the test formulation of the present disclosure and treatment 2 using the concomitant administration of the three API according to some embodiments.

Figure 3:
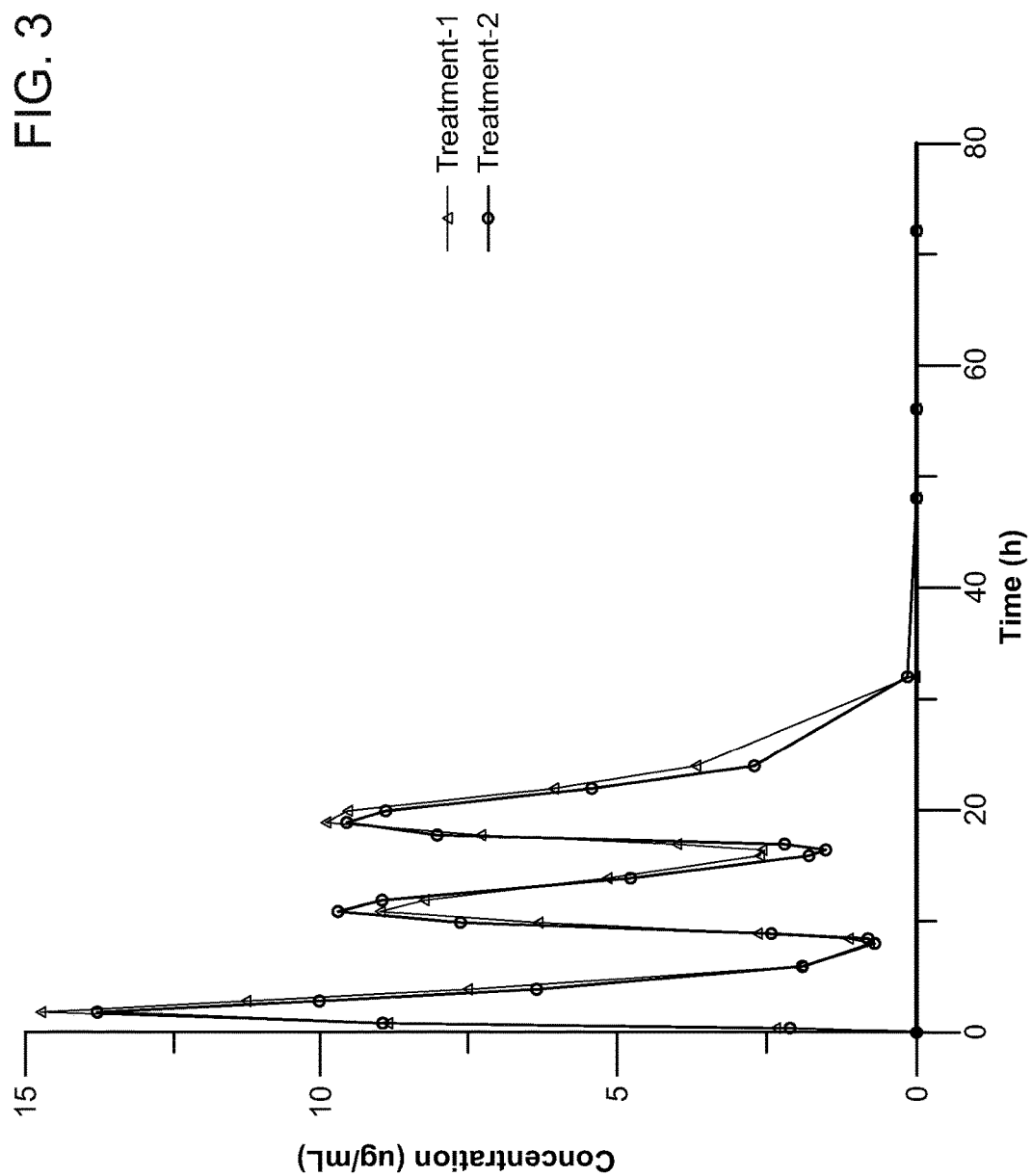

FIG. 3 illustrates the linear profile of the mean for amoxicillin in treatment 1 using the test formulation of the present disclosure and treatment 2 using the concomitant administration of the three API according to some embodiments.

Figure 4:
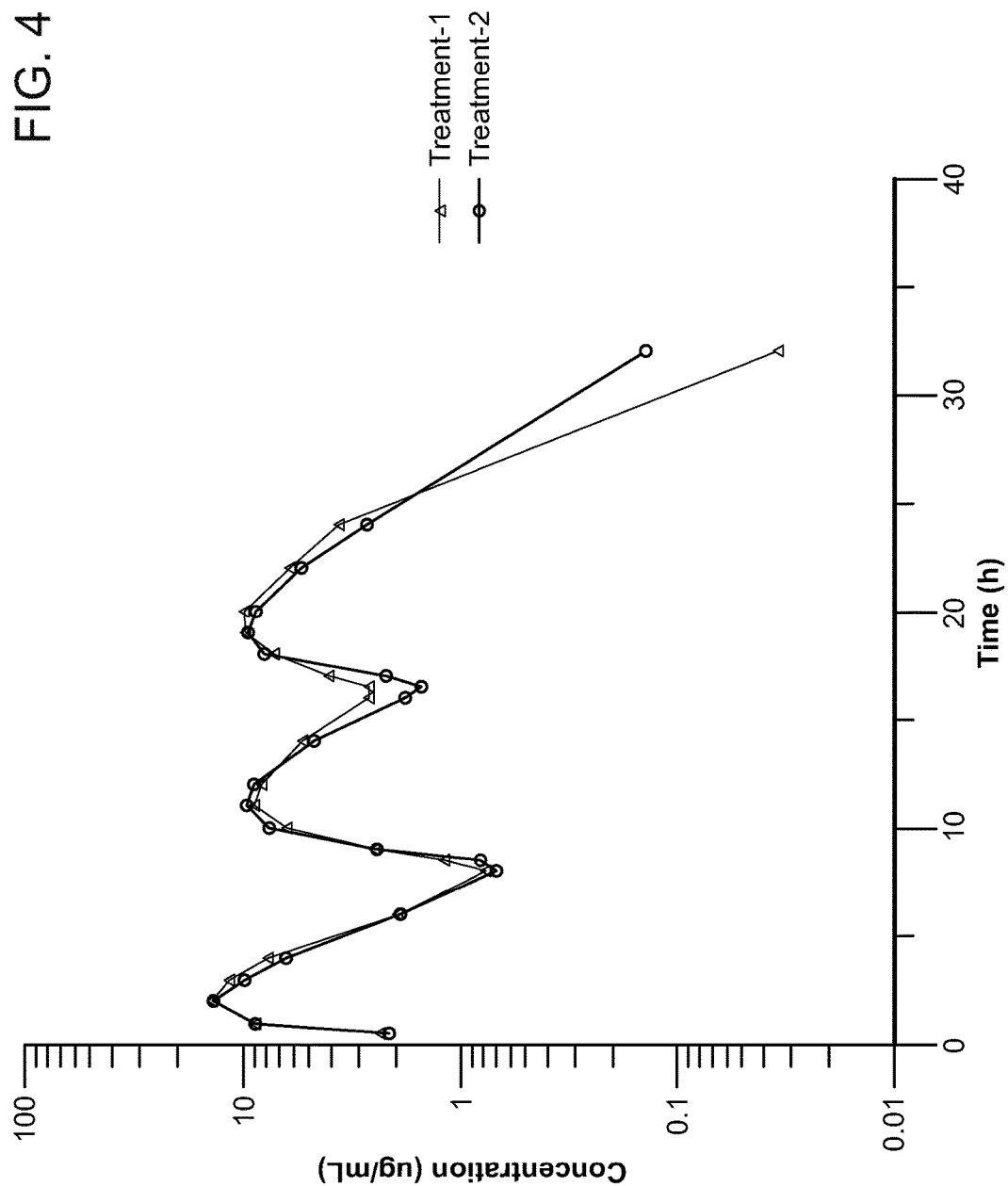

FIG. 4 illustrates the logarithmic profile of the mean for amoxicillin in treatment 1 using the test formulation of the present disclosure and treatment 2 using the concomitant administration of the three API according to some embodiments.

Figure 5:
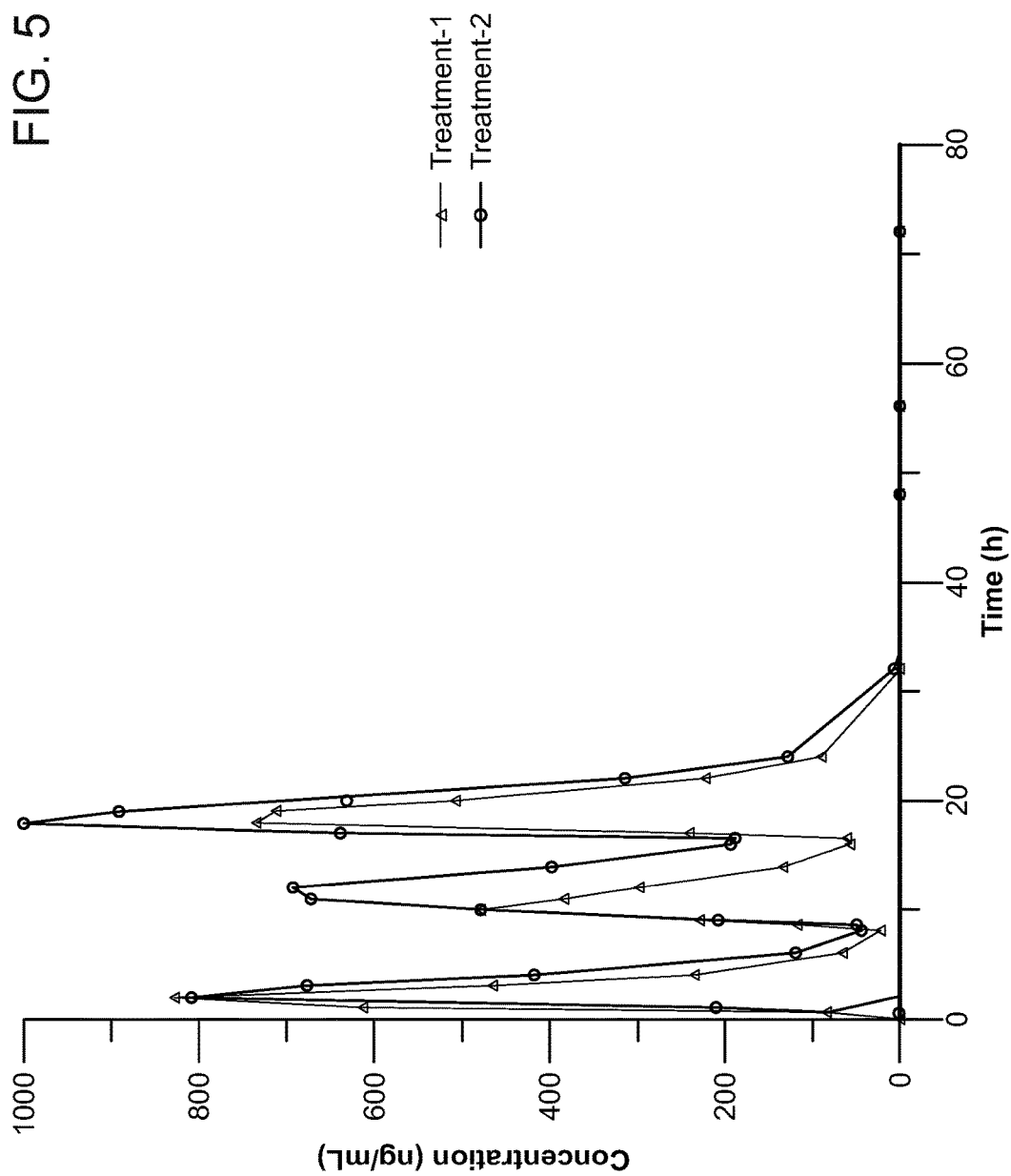

FIG. 5 illustrates the linear profile of the mean for omeprazole in treatment 1 using the test formulation of the present disclosure and treatment 2 using the concomitant administration of the three API according to some embodiments.

FIG. 6 illustrates the logarithmic profile of the mean for omeprazole in treatment 1 using the test formulation of the present disclosure and treatment 2 using the concomitant administration of the three API according to some embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

*Helicobacter pylori* is a common and important transmissible (human-to-human) bacterial human pathogen usually through oral-oral routes. *Helicobacter pylori* (*H. pylori*) is a Gram-negative, microaerophilic rod that can inhabit in the mucous membranes lining the stomach of human or other animals.

The prevalence of this infection varies worldwide from as low as 10% in some developed western nations to higher than 80% among the indigent populations of many developing countries. The World Health Organization (WHO) estimates that *H. pylori* is present in about half of the world's population while the Centers for Disease Control and Prevention (CDC) estimates a total of 30-40% of Americans harbor the infection, with the highest prevalence rates in minority subgroups.

The major concerns of *H. pylori* as an infectious agent are that the agent can be continuously infectious throughout an initial, clinically latent and often asymptomatic stage, and it can induce a pattern of acute-on-chronic gastric inflammation, resulting in disordered gastric physiology and progressive gastric mucosal damage. In addition, the agent can produce serious pathological effects and clinical sequelae in infected patients.

Patients with *H. pylori* infection may present with mild dyspepsia. One of the major current reasons for *H. pylori* testing is the presence of dyspepsia, as many *H. pylori*-related diseases are associated with this symptom. In addition, it has been shown that more than 50% of dyspeptic patients with no evidence of ulcer disease (non-ulcer dyspepsia or functional dyspepsia) are infected with *H. pylori* and are at risk for progression of gastric mucosal damage.

Persistent infection with *H. pylori* is strongly associated with chronic active gastritis, peptic ulcer, non-ulcer dyspepsia, GERD, gastric ulcer, duodenal ulcer as well as with gastric carcinoma, gastric adenocarcinoma, and MALT lymphoma (MALToma). *H. pylori* can persist for decades or even the whole life of the subject unless eradicated by proper treatment.

In 1994, *H. pylori* was classified as a Group 1 agent (carcinogenic to humans) by the WHO's International Agency for Research on Cancer and it is now accepted as a major cause of gastric cancer worldwide. Gastric cancer is amongst the most frequent cancers worldwide and is associated with a poor prognosis (5-year survival rate of only 10-15% in patients with advanced disease). In the first half of the 20th century, gastric cancer was the most common cancer in many Western countries including the United States of America (USA). As such, identification and eradication of *H. pylori* before pre-neoplastic lesions are present is vital if gastric cancer is to be prevented. For example, population-based eradication of *H. pylori* in an area where the infection is endemic (Taiwan) showed a 67% reduction in new ulcers, 77% reduction in the incidence of gastric atrophy, and 25% reduction in gastric cancer, comparing the period before (1995-2003) to the *H. pylori* eradication period (2004-2008).

*H. pylori* infection outcomes are many and include: dyspepsia (non-ulcer or functional), peptic ulcer disease (duodenal ulcer and gastric ulcer), primary gastric B-cell lymphoma, gastric cancer, vitamin B12 deficiency, and iron deficiency anemia.

Dyspepsia (defined as recurrent pain or discomfort centered in the upper abdomen often with a relation to meals) is a common and perplexing global problem affecting 15% to 40% of the population. It is estimated that as many as 50% of non-ulcer or functional dyspeptic patients are infected with *H. pylori*. *H. pylori* eradication at this stage confers significant clinical and economic benefits, including prevention and cure of unrecognized peptic ulcers, and reduction in the risk of developing gastric cancer.

Gastric cancer is the second most frequent cancer worldwide and is associated with a poor prognosis (5-year survival rate of only 10-15% in patients with advanced disease). The National Cancer Institute [NCI] (Surveillance Epidemiology and End Results [SEERS]) estimates that >21,000 Americans will be diagnosed with and almost 11,000 will die of gastric cancer in 2012 (NCI 2012). Almost all gastric cancer is now known to be attributable to *H. pylori* infection (i.e. recent studies have confirmed that gastric cancer develops in patients infected with *H. pylori* but not in uninfected persons). Moreover, it has been shown that *H. pylori* eradication halts the natural progression of atrophic gastritis and either eliminates, stabilizes, or reduces risk for progression to gastric cancer, depending upon the severity and extent of damage present when the *H. pylori* infection is cured.

The benefits of *H. pylori* eradication at any stage of *H. pylori* infection are clear; however, it is evident that identification and eradication of *H. pylori* before the development of atrophic gastritis is associated with the most positive clinical outcomes.

A combination therapy in which two antibiotics and an antacid, such as proton pump inhibitor (PPI), are ingested as separate dosage forms has been commonly used for *H. pylori* eradication therapy. It has however been shown that the commonly used combination therapy was not as efficient in *H. pylori* eradication therapy. If the patients have good compliance, the eradication rate (>85%) can be achieved after 7 to 14 days of treatment. However, a major drawback of the combination therapy (also known as triple therapy) is possibly due to poor compliance. Patients undergoing combination therapy are commonly given on average 5 tablets twice daily. In the standard triple therapy, the *helicobacter*-inhibiting anti-microbial agent(s) and a proton pump inhibitor (PPI) are usually administered concurrently, for example, within about 1 hour of each other or co-administered as separate dosage forms. In addition, instability of the active agents in the patient's stomach can result in poor absorption and insufficient dosage. Furthermore, *H. pylori* strains have been shown to be resistant to clarithromycin or metronidazole, which are the standard anti-microbial agents used in the standard triple-therapy leading to therapeutic failures. Additionally, taking multiple separate drugs during the therapy increase the compliance and adherence risk associated with concomitant medication and greatly influence the impacts on treatment tolerability and increase variability.

Currently approved triple combination therapies often achieve sub-optimal eradication. Two separate meta-analyses have demonstrated that effectiveness of both clarithromycin and metronidazole-based triple therapies has decreased to unacceptably low levels of <80% effectiveness.

There is growing consensus among the scientific and medical communities that the currently approved therapies for the eradication of *H. pylori* no longer provide adequate therapy for over 20% of treated patients. The potential morbidity of *H. pylori* infection may range from non-serious to life-threatening disease states. Indeed, ineffective treatment may lead to generally increased bacterial resistance, such as clarithromycin and metronidazole resistant *H. pylori* strains, as well as complicate future treatment attempts to eradicate the *H. pylori* infection and thus cause greater medical and financial burdens.

Aspects of the invention relate to a new highly effective first-line therapy that can reduce treatment burden on the patient. In some embodiments, the methods and compositions of the invention are useful to achieve a high rate of eradication of *H. pylori*.

Some aspects of the invention relate to pharmaceutical compositions for the treatment of a disorder associated with a *H. pylori* infection in a subject. In particular, the pharmaceutical composition is a single dosage form comprising one or more anti-microbial agent(s), such as antibiotics or antibacterial agents, and a proton pump inhibitor. Aspects of the invention relate to pharmaceutical compositions formulated to have optimal pharmacokinetic properties to deliver the active agents in a single dosage form. In particular, such pharmaceutical compositions can have a relatively fast release (i.e. immediate release) of the antibiotic agents to ensure gastric absorption and a modified or delayed release of the proton pump inhibitor to ensure intestinal absorption.

The mechanism of action of the antimicrobial agents, or antibiotics, in the case of *H. pylori*, is thought to be both local at the site of infection in the gastric tissue, and systemic, including via reuptake of the antimicrobial agents to gastric tissue from the blood. As such, gastric release of the antibiotics is essential for effective treatment. However, antibiotics are generally more stable in mildly acidic to basic condition, and can sensitive to degradation of gastric acid. The proton pump inhibitors (PPIs) are drugs capable of reducing gastric acid production by, for example, inhibiting the hydrogen/potassium adenosine triphosphatase enzyme system of the gastric parietal cell. Therefore, addition of PPI which suppresses the production of stomach acid can increase intragastric pH, decrease the degradation of the antibiotics to further help the anti-*H. pylori* effects. PPIs are however acid-unstable and can be sensitive to degradation by gastric acid. The PPI, in the compositions of the present invention is formulated for intestinal release to avoid its rapid degradation in the acidic gastric environment.

"Active Pharmaceutical Ingredient" or API as used herein refers to the molecular/chemical moiety, responsible for bringing about a therapeutic response in mammal. API as used herein includes pharmaceutically acceptable salts, stereoisomers and mixtures of stereoisomers, solvates (including hydrates), polymorphs, and/or esters thereof. The term "salts" refers to the product formed by the reaction of a suitable inorganic or organic acid or base with the "free base or acid" form of the API.

As used herein the "core" or "dosage core" refers to the internal active and inactive pharmaceutical ingredients of the dosage form and that forms the pharmaceutical composition. As used herein the "dosage composition" refers to the internal active and inactive pharmaceutical ingredients of the dosage form that forms the pharmaceutical composition. The terms dosage composition and dosage core can be used interchangeably. The dosage composition, in some embodiments, can be coated. The dosage composition includes, but is not limited to, a bead, pellet, microgranule, granulate, mini-tablet, drug crystal, etc., having a size typically in the range of from about 100 μm to about 2 mm or more including all subranges therebetween.

As used herein "encapsulation" or "encapsulated" or "encapsulating" refers to the coating of an agent or dosage form, such as an active pharmaceutical ingredient (API) by at least on layer. As such, the terms "coating" as used herein also refers to "layering" and "encapsulating" and the terms "coating" "layering" and "encapsulating" can be used interchangeably. An encapsulated product can be in the form of a granule, tablet, minitablets, a capsule and the like.

"Stability" or stabilization or stabilized as used herein refers to preservation of the active pharmaceutical ingredient(s), such as, for example, proton pump inhibitor, antibiotic, anti-microbial agent and prevention of its conversion into degradation variants, in the dosage forms of the invention.

"Dosage form" as used herein refers to suitable physical form like capsules, tablet, sachets and the like, which are convenient for administration of drug to patient in need of that drug. The term dosage form can be used interchangeably with composition and/or formulation.

Compositions

Some aspects of the invention relate to pharmaceutical compositions comprising (1) an immediate release first dosage composition comprising of at least two antibiotics; (2) a delayed release second dosage composition comprising a proton pump inhibitor and a coating; and (3) an outer layer encapsulating the first dosage and the second dosage compositions. In some embodiments, the coating on the second dosage composition is designed to meet the two stage test dissolution profile in a basket apparatus:

(a) release of not more than 10% of the proton pump inhibitor in 120 min in an acid stage comprising 900 ml 0.1N HCl at 100 rpm; and (b) release of not less than 75% of the proton pump inhibitor in 45 min in 900 ml phosphate buffer pH 6.8 at 100 rpm following the acid stage.

In some embodiments, the coating on the second dosage composition is designed to meet the two stage test dissolution profile in a paddle apparatus:

(a) release of not more than 10% of the proton pump inhibitor in 120 min in an acid stage comprising 900 ml 0.1N HCl at 100 rpm; and (b) release of not less than 75% of the proton pump inhibitor in 45 min in 900 ml phosphate buffer pH 6.8 at 100 rpm following the acid stage.

In some embodiments, the outer layer encapsulating the first composition and the second composition is carrier member that houses the first and the second dosage compositions.

According to some aspects, the antibiotics and the proton pump inhibitors can be provided in a formulation designed to yield improved pharmacokinetic properties. The present pharmaceutical composition can reduce unwanted degradation of the antibiotics and of the proton pump upon administration. In addition, the present composition can have the advantage that the dosage of each agent can be reduced, compared to clinically standard doses. Additional advantages can include a reduction in the possibility of side effects, a reduction in cost, and a reduction in the duration of treatment.

In some embodiments, the immediate release first dosage composition can comprise at least one antibiotic and an antibacterial agent. In some embodiments, the immediate release first dosage composition can comprise at least two antibiotics.

In some embodiments, the pharmaceutical composition comprises a combination of rifabutin, amoxicillin as antibiotics and omeprazole as the proton pump inhibitor.

According to some aspects, the pharmaceutical compositions of the present invention may be used specifically in treating disorders associated with *H. pylori* or to prevent the recurrence of disorders associated with *H. pylori*. The pharmaceutical compositions may be used to inhibit, stabilize, or reduce the risk for progression to gastric cancer.

Antibiotics and Antibacterial Agents

The present compositions may comprise at least one antibacterial agent. The antibacterial agents may be selected from a number of suitable antibiotics known in the art. In some embodiments, the antibacterial agent is an antibiotic as described herein. In some embodiments, the antibiotics and/or antibacterial agents are formulated in an immediate release first dosage composition.

As used herein, the term "immediate release" (IR) refers to release of greater than or equal to about 50%, greater than or equal to about 60%, greater than or equal to about 70%, greater than or equal to about 80%, greater than or equal to about 90%, or greater than or equal to about 95% of the drug within about 2 hours, or in other embodiments within about one hour or less following administration of the dosage form. As used herein, the term "immediate-release composition" refers to a dosage composition as defined herein comprising an API. In some embodiments, the immediate release composition can optionally comprise a coating, wherein the optional coating functions to protect the immediate-release core from contact with a different API, but does not modify substantially the release properties. Immediate-release compositions have immediate release properties as described herein.

In some embodiments, the at least two antibiotics are released within about 1 hour, or within about 2 hours of administration of the pharmaceutical composition. In some embodiments, at least 70% of the at least one antibiotic is released between 5 and 120 min. following oral administration of the composition.

In some embodiments, the amoxicillin is released within about 1 hour, or within about 2 hours of administration of the pharmaceutical composition. In some embodiments, the mean plasma concentration of amoxicillin after administration to healthy patients is 2.377 µg/ml at 0.5 hour, 8.918 µg/ml at 1 hour, 14.733 µg/ml at 2 hour, and 11.253 µg/ml at 3 hours.

In some embodiments, an average of no less than 80% of amoxicillin is released in 60 min at 100 rpm in a baskets apparatus (900 ml 0.01 N HCl, at 100 rpm in a baskets apparatus). In some embodiments, an average of 90%, 96%, and 97% of the amoxicillin is released in an in vitro dissolution assay at 20, 30, and 45 minutes, respectively.

In some embodiments, the rifabutin is released within about 1 hour, or within about 2 hours of administration of the pharmaceutical composition. In some embodiments, the mean plasma concentration of rifabutin after administration to healthy patients is 5.52 ng/ml at 0.5 hour, 28.07 ng/ml at 1 hour, 66.06 ng/ml at 2 hour, and 72.49 ng/ml at 3 hours.

In some embodiments, an average of no less than 75% of rifabutin is released in 45 min at 100 rpm in a baskets apparatus (900 ml 0.01 N HCl, at 100 rpm in a baskets apparatus). In some embodiments, an average of 95, 97, and 98% of the rifabutin is released in an in vitro dissolution assay at 20, 30, and 45 minutes, respectively.

In some embodiments, the antibiotic agents may include, but are not limited to, ansamycin, amoxicillin, any pharmaceutically acceptable salt thereof, solvates thereof, and any combinations of the foregoing.

In some embodiments, the antibiotic agent may be an ansamycin selected from the group consisting of rifamycin, rifaximin, rifampicin, rifabutin, pharmaceutically acceptable salts thereof, solvates thereof, and any combinations of the foregoing. Ansamycin antibiotic may comprise rifampicin and/or its semi-synthetic derivative, rifabutin. More typically, the ansamycin can be rifampicin, rifabutin or a combination thereof.

Rifabutin and rifampicin inhibits bacterial DNA-dependent RNA synthesis by inhibiting the DNA-dependent RNA-polymerase of the bacteria. Rifabutin has been shown to have potential utility in treating *H. pylori* as it does not share resistance with clarithromycin.

Resistance of *H. pylori* to amoxicillin or rifabutin is very rare. The mean rate of *H. pylori* resistance to rifabutin (calculated from 11 studies including 2982 patients) was 1.3% in general and 0.6% for patient's naïve to *H. pylori* eradication treatment.

In some embodiments, the pharmaceutical composition may also comprise at least one or more further antibacterial or antibiotic agents. For example, the antibiotic agent or antibacterial agent can be one of penicillins, bismuth compounds, tetracyclines, nitroimidazoles, quinolones, lincosamides, macrolides and cephalosporins, any pharmaceutically acceptable salt thereof, solvates thereof, and any combinations of the foregoing.

Examples of the penicillins include, but are not limited to, penicillin G, penicillin V, pheneticillin, propicillin, methicillin, oxacillin, cloxacillin, dicloxacillin, flucloxacillin, nafcillin, ampicillin, amoxycillin, bacampicillin, hetacillin, metampicillin, pivampicillin, talampicillin, carbenicillin, carfecillin, carindacillin, sulbenicillin, ticarcillin, azlocillin, mezlocillin, piperacillin, apalcillin, temocillin, mecillinam and pivmecillinam, any pharmaceutically acceptable salt thereof, solvates thereof, and any combinations of the foregoing.

Examples of bismuth compounds include, but are not limited to, bismuth subcitrate, bismuth aluminate, bismuth oxide, bismuth salicylate, bismuth sugballate, bismuth tannate, bismuth phosphate, bismuth tribromphenate, bismuth subcarbonate, bismuth subnitrate, and mixtures, any pharmaceutically acceptable salt thereof, solvates thereof, and any combinations of the foregoing.

Examples of the tetracyclines include, but are not limited to, tetracycline hydrochloride, oxytetracycline, doxycycline, methacycline, chlortetracycline, demeclocycline and minocycline and, pharmaceutically acceptable salt thereof, solvates thereof, and any combinations of the foregoing.

Examples of nitroimidazoles include metronidazole, tinidazole, nimorazole, ornidazole and orthanidazole, any pharmaceutically acceptable salt thereof, solvates thereof, and any combinations of the foregoing.

Examples of quinolones include, but are not limited to, ciprofloxacin, norfloxacin, enoxacin, lomefloxacin, pefloxacin, amifloxacin, fleroxacin, levofloxacin, nadifloxacin, rufloxacin, sparfloxacin, tosufloxacin and ofloxacin, any pharmaceutically acceptable salt thereof, solvates thereof, and any combinations of the foregoing.

Examples of lincosamides include, but are not limited to, lincomycin and clindamycin, any pharmaceutically acceptable salt thereof, solvates thereof, and any combinations of the foregoing.

Examples of macrolides include, but are not limited to, erythromycin, spiramycin, oleandomycin, triacetyloleandomycin, clarithromycin, roxithromycin, josamycin, kitsamycin, midecamycin, miocamycin, rokitamycin, dirithromycin, rosarimycin, flurithromycin and azithromycin, any pharmaceutically acceptable salt thereof, solvates thereof, and any combinations of the foregoing.

Examples of cephalosporins include, but are not limited to, cephalexin, pivcephalexin, cephalothin, cephazolin, cefroxadine, cefadroxil, cefatrizine, cefaclor, cefprozil, cephradine, and second as well as third generation cephalosporins such as cephamandole, cefuroxime, cefuroxime axetil, cefonicid, ceforanide, cefotiam, cefotaxime, cefmenoxime, cefodizime, ceftizoxime, cefiximine, cefdinir, cefetamet pivoxil, cefpodoxime proxetil, ceftibuten, ceftazidime, ceftoperazone, cefpiramide, cefsoludin, cefepime, cefpirome and ceftriaxone, and related compounds such as oxycephalosporins including latamoxef, and cephamycins such as cefoxitin, cefmetazole, cefotetan, cefbuperazone and cefminox, any pharmaceutically acceptable salt thereof, solvates thereof, and any combinations of the foregoing.

In some embodiments, rifabutin can be used in combination with penicillin as a first antibiotic, and a bismuth compound, as a second antibacterial agent. In some embodiments, an alternative second antibacterial agent can be a tetracycline.

In some embodiments, rifabutin can be used in combination with amoxicillin. In some embodiments, the antibiotic combination can have synergistic activity to produce a synergistic anti-bacterial effect. In some embodiments, the antibiotic combination can result in a synergistic post antibiotic effect (PAE) such as inhibition or delayed regrowth of H. pylori following exposure to the antibiotic combination. This factor can allow for the continued eradication of the bacteria after termination of the therapy.

Rifabutin

Rifabutin is a derivative of rifamycin S, belonging to the class of ansamycins. The rifamycins owe their antimycobacterial efficacy to their ability to penetrate the cell wall and to their ability to complex with and to inhibit DNA-dependent RNA polymerase. Rifabutin has been found to interact with and to penetrate the outer layers of the mycobacterial envelope.

Rifabutin is indicated for the prevention of disseminated M. avium complex (MAC) disease in patients with advanced HIV infection (CD4+ cell count ≤200/mm3 with an AIDS defining diagnosis, or CD4+ cell count ≤100/mm$^3$ without an AIDS defining diagnosis). It is recommended that 300 mg of rifabutin be administered once daily with or without food. For those patients who experience nausea, vomiting or other gastrointestinal upsets, it may be useful to split the rifabutin dose in half (one 150 mg capsule) twice a day with food.

Following oral administration, at least 53% of rifabutin dose is rapidly absorbed with rifabutin peak plasma concentrations attained in 2 to 4 hours. High-fat meals slow the rate without influencing the extent of absorption of rifabutin from the capsule dosage form. The mean (±SD) absolute bioavailability assessed in HIV positive patients in a multiple dose study was 20% (±16%, n=5) on day 1 and 12% (±5%, n=7) on day 28. In healthy adult volunteers administered a single oral dose of 300 mg of rifabutin, the mean (±SD) peak plasma concentration ($C_{max}$) was 375 (±267) ng/mL (range: 141 to 1033 ng/mL). Mean rifabutin steady-state trough levels ($C_p$, $C_{minss}$, 24-hour post dose) ranged from 50 to 65 ng/mL in HIV positive patients and in healthy normal volunteers.

Pharmacokinetic dose-proportionality over the 300 to 900 mg single dose range has been demonstrated in early symptomatic HIV positive patients and in healthy normal volunteers over the 300 to 600 mg single dose range.

Rifabutin appears to be widely distributed throughout the body and has been detected in all tissues and body fluids examined. Concentrations several fold greater than those achieved in plasma have been observed in lung parenchyma, gall bladder and the small intestinal wall. The apparent volume of distribution at steady-state (Vss) estimated in early symptomatic HIV positive male patients following IV dosing was large (8 to 9 L/kg), suggesting extensive distribution of rifabutin into the tissues. About 85% of the drug is bound to plasma proteins over a concentration range of 50 to 1000 ng/ml. Binding is predominantly to human serum albumin, is concentration independent and does not appear to be influenced by renal or hepatic dysfunction.

Rifabutin undergoes extensive oxidative metabolism. Of the 5 metabolites that have been identified, 25-O-desacetyl-rifabutin and 31-hydroxyrifabutin are the most predominant and show a plasma metabolite: parent area under the curve ratio of 0.10 for 25-O-desacetylrifabutin and 0.07 for 31-hydroxyrifabutin metabolite. The 25-O-desacetylrifabutin metabolite has antimycobacterial activity equal to the parent drug and contributes up to 10% to the total antimicrobial activity. The 31-hydroxy metabolite has some antimicrobial activity ($\frac{1}{16}$ that of parent drug), but, considering its concentration in plasma, it is probably not contributing significantly to the therapeutic activity of rifabutin. Rifabutin can induce its own metabolism on multiple dosing.

The area under the plasma rifabutin concentration-time curve (AUC) following multiple dosing decreased by 38%, but its terminal half-life remained unchanged. The plasma elimination profile of rifabutin is biphasic with an initial half-life of approximately 4 hours followed by a mean terminal half-life of 45 (±17) hours (range: 16 to 69 hours). Mean systemic clearance in healthy adult volunteers following a single oral dose was 0.69 (±0.32) L/hour/kg (range: 0.46 to 1.34 L/hour/kg). Rifabutin is mainly excreted in the urine, primarily as metabolites and to a lesser extent in the feces. Fifty-three percent (53%) of the oral dose of $^{14}$C-labelled drug was recovered in the urine by 5 days post-dose and 30% was recovered in the feces over the same period. Renal and biliary excretion of the unchanged drug each contributes approximately 5% to the systemic clearance.

The most common adverse events, reported more frequently in the rifabutin treated patients than in the placebo group were: urine discoloration, neutropenia, skin rash, nausea and/or vomiting, and abdominal pain.

Based on information available, the pharmacokinetic parameters observed after a single oral 150 mg dose of rifabutin capsules under fasting conditions summarized in Table 1:

TABLE 1

Expected Pharmacokinetic Parameters of Rifabutin and its Metabolite

| Pharmacokinetic (PK) parameters | Rifabutin | 25-O-Desacetylrifabutin |
|---|---|---|
| $C_{max}$ (ng/ml)* | 188 | 27 |
| $T_{max}$ (hours) | 3 | — |
| $T\frac{1}{2}_{el}$ (hours) | 40 | — |

*Assuming linearity, for a 50 mg dose of rifabutin, the expected $C_{max}$ should be about 63 ng/mL and 9 ng/mL for rifabutin and 25-O-desacetylrifabutin, respectively.

Amoxicillin

Amoxicillin, a semisynthetic penicillin of the aminopenicillin group, is bactericidal against sensitive organisms. It acts through the inhibition of peptidoglycan synthesis in the bacterial cell wall. This leads to the formation of a defective cell wall with eventual lysis and death to the cell.

Amoxicillin is given orally and because it is stable in the presence of gastric acid, it may be given without regard to meals. The duration of therapy depends on the type and severity of the infection, and can vary from 7 to 10 days to several weeks.

Amoxicillin is rapidly absorbed after oral administration and is stable in the presence of gastric acid. Peak serum concentrations are usually attained within 1 to 2 hours following oral administration and are generally 2 to 2.5 times greater than those obtained with an equivalent dose of oral ampicillin. The peak plasma concentration ranged from 2.65 to 5.75 µg/ml after administration of a single dose of 250 mg of reconstituted amoxicillin granules suspension. Oral amoxicillin has better bioavailability than oral ampicillin. Amoxicillin diffuses readily into most body tissues and fluids, e.g., middle ear fluid, synovial fluid. Amoxicillin is not highly protein bound. Its elimination half-life ranges from 0.7 to 1.4 hours in patients with normal renal function and 7 to 10 hours in patients with impaired renal function. Amoxicillin is partially metabolized to inactive metabolites and then rapidly excreted in urine. Small amounts of the compounds are excreted in feces and bile.

The following adverse effects have been reported with the use of amoxicillin: nausea, vomiting, diarrhea, anorexia, epigastric distress, gastritis, black hairy tongue, glossitis, stomatitis, hematologic related reactions, rash and moderate rise in hepatic enzymes.

Based on information available, the pharmacokinetic parameters observed after a single oral 1000 mg dose of amoxicillin capsules under fasting conditions are summarized in Table 2:

TABLE 2

Expected Pharmacokinetic Parameters of Amoxicillin

| Pharmacokinetic (PK) parameters | Amoxicillin |
|---|---|
| $C_{max}$ (µg/ml) | 14 |
| $T_{max}$ (hours) | 1.65 |
| $T\frac{1}{2}_{el}$ (hours) | 1.15 |

Proton Pump Inhibitors

Omperazole

Omeprazole is an oral antiulcer agent. It is indicated in the treatment of conditions where a reduction of gastric acid secretion is required, such as: duodenal ulcer; gastric ulcer; NSAID-associated gastric and duodenal ulcers; reflux esophagitis; symptomatic gastroesophageal reflux disease, i.e., heartburn and regurgitation; dyspepsia; Zollinger Ellison syndrome (pathological hypersecretory condition); eradication of *H. pylori*. The usual recommended adult oral dose ranges between 10 and 40 mg per day.

Omeprazole belongs to a class of antisecretory compounds that suppress gastric acid secretion by specific inhibition of the $H^+/K^+$ ATPase enzyme system at the secretory surface of the gastric parietal cell. Because this enzyme system is regarded as the acid (proton) pump within the gastric mucosa, omeprazole has been characterized as a proton pump inhibitor, in that it blocks the final step of acid production. This effect is dose related and leads to inhibition of both basal and stimulated acid secretion irrespective of the stimulus.

Omeprazole is absorbed rapidly. After an initial oral dose of omeprazole, approximately 35% of the drug is absorbed from the gastrointestinal tract. Absorption takes place in the small intestine and is usually completed within 4 hours. The plasma protein binding of omeprazole is about 95%.

Peak plasma concentrations of omeprazole and AUC are approximately proportional to doses up to 40 mg, but because of a saturable first-pass effect, a greater than linear response in peak plasma concentration and AUC occurs with doses greater than 40 mg. The antisecretory effect of omeprazole is directly proportional to the AUC; it is not dependent on the plasma concentration at any given time. Omeprazole undergoes first-pass metabolism by the cytochrome P-450 system, mainly in the liver, through CYP 2C19 and CYP 3A4. The CYP 2C19 isozyme, which is involved in the metabolism of all available proton pump inhibitors, exhibits polymorphism. Approximately 3% of the Caucasian population and 15-20% of Asian populations lack a functional CYP 2C19 enzyme and are called poor metabolisers.

The average half-life of the terminal phase of the plasma concentration-time curve is approximately 40 minutes. Following IV and oral administration of omeprazole, 80% of the dose is recovered as urinary metabolites. The remaining 20% is excreted in the feces.

The omeprazole capsule (as a multiple unit formulation) is usually emptied gradually from the stomach into the intestine. In contrast to the capsule, the tablet (as a single unit formulation) will enter the intestine and dissolve as one unit. Consequently, the absorption and first pass metabolism of the tablet take place only during a very limited period. This may be one of the reasons for the difference observed in the pharmacokinetic variables of the formulation according to the embodiments of the invention (Treatment 1) and the omeprazole capsule (Treatment 2).

Omeprazole is well tolerated. Most adverse reactions have been mild and transient and there has been no consistent relationship with the treatment. The following adverse events have been reported in patients receiving omeprazole capsules in controlled clinical situations: diarrhea, headache, flatulence, abdominal pain, constipation, nausea and vomiting.

Based on data available, the pharmacokinetic parameters observed after a single oral 40 mg dose of omeprazole delayed-release capsules under fasting conditions are summarized in Table 3:

TABLE 3

Expected Pharmacokinetic Parameters of Omeprazole

| Pharmacokinetic (PK) parameters | Omeprazole |
|---|---|
| $C_{max}$ (ng/ml) | 1050 (Inter CV 55%) |
| $T_{max}$ (hours) | 1.75 |
| $T\frac{1}{2}_{el}$ (hour) | 1 |

In some embodiments, the composition comprises at least one proton pump inhibitor. Proton pump inhibitors (PPIs) are highly effective gastric secretion inhibitors. The at least one proton pump inhibitor may be selected from one or a combination of the group including omeprazole, pantoprazole, lansoprazole, ilaprazole, dexlansoprazole, esomeprazole and rabeprazole, any pharmaceutically acceptable salt thereof and solvates thereof. In some embodiments, the proton pump inhibitor may include a further agent such as magnesium, sodium bicarbonate or sodium.

In some embodiments, the proton pump inhibitor is omeprazole. Omeprazole is a proton pump inhibitor that suppresses gastric acid secretion by specific inhibition of the H+/K+-ATPase in the gastric parietal cell. By acting specifically on the proton pump, omeprazole blocks the final step in acid production, thus reducing gastric acidity. In some embodiments, the proton pump inhibitor may comprise omeprazole magnesium.

It would be understood that stability of the PPI, such as omeprazole, is a function of pH and that the PPI can be rapidly degraded in acidic condition, for example in the stomach of the patient. One of skill in the art would appreciate that omeprazole would not be able to inhibit gastric acid secretion in acidic condition if it was to act on the stomach directly. In addition, under such gastric acidic conditions, the efficacy of antibiotics to eradicate H pylori would be decreased.

In some embodiments, an enteric coating can be applied over the PPI dosage composition (e.g. omeprazole) to delay its release and minimize undesired degradation by preventing the PPI core from contacting the acidic pH conditions of the stomach. The enteric coating allows the absorption of the PPI such as omeprazole to take place in the small intestine and and inhibits the contact with gastrin from the gastric mucosa.

In some embodiments, the proton pump inhibitor composition is formulated to have a modified release profile. For example, the proton pump inhibitor can be formulated to have an enteric coating. As used herein, the term "modified release" coating encompasses coatings that delay release, sustain release, extend release, prevent release, minimize release and/or otherwise prolong the release of a drug relative to formulations lacking such coatings which release a drug relatively quickly (i.e., "immediate release" compositions). The term "modified release" encompasses "sustained release," "extended release," "delayed release," and the like. The term "modified release" is used interchangeably with "controlled release" or "delayed release". The term "modified-release" or "delayed release" dosage composition refers broadly to a dosage form showing one or more modified-release properties, as described herein.

The term "lag time" refers to a time period immediately after administration of the drug-containing particle wherein less than about 10%, for example less than about 9%, less than about 8%, less than about 7%, less than about 6%, less than about 5%, less than about 4%, less than about 3%, less than about 2%, less than about 1%, or more substantially about 0%, of the drug is released from a particle.

The terms "enteric coating" or "delayed release coating" as used herein, are used interchangeably and refers to a pH sensitive coating that is resistant to gastric juice (i.e., relatively insoluble at the low pH levels found in the stomach), and which dissolves at the higher pH levels found in the intestinal tract. The gastrointestinal tract is responsible for ingestion, digestion, absorption and waste elimination. The stomach is part of the upper gastrointestinal tract. The intestinal tract, or lower gastrointestinal tract, comprises the small intestine and large intestine. Enteric refers to the small intestine; enteric behavior refers to coatings that promote the release of medication in the small intestine. In some embodiments, a lag time of about 2 to about 4 hours is achieved by coating the particle with an enteric coating.

In some embodiments, the proton pump inhibitor is released about 2 hours or more following administration of the pharmaceutical composition. In some embodiments, the delayed release second dosage composition comprising the PPI has at least one outer layer ensuring that the release of the proton pump inhibitor is delayed from 120 to 240 minutes. In some embodiments, at least 70% of the PPI is released between 120 and 240 min. following oral administration of the composition.

In some embodiments, the PPI is released within about 1 hour, or within about 2 hours of administration of the pharmaceutical composition. In some embodiments, the mean plasma concentration of omeprazole after administration to healthy patients is 85.80 ng/ml at 0.5 hour, 612.96 ng/ml at 1 hour, 827.65 ng/ml at 2 hour, and 465.59 ng/ml at 3 hours.

In some embodiments, an average of 0% of omeprazole is released in an acid stage (pH1), and 90, 90, and 86% of the omeprazole is released in an in vitro dissolution assay at 20, 30, and 45 minutes following the acid stage, respectively. In some embodiments, not more than 10% of the proton pump inhibitor is released in an acid stage (900 ml 0.1N HCl at 100 rpm, pH1), and not less than 75% of the proton pump inhibitor is released in an in vitro dissolution assay (900 ml phosphate buffer pH 6.8 at 100 rpm) at 45 minutes following the acid stage.

In some embodiments, the delayed release second dosage composition further comprises a buffering agent in an amount sufficient to inhibit or reduce degradation of at least some of the proton pump inhibitor. Suitable pH adjusting agents include, but are not limited to, meglumine, sodium bicarbonate, calcium carbonate or sodium sulphate or combinations thereof.

In some embodiments, the delayed release second dosage composition comprising the PPI further comprises a time delay agent. Suitable time delay agents include, but are not limited to, glyceryl monostearate, glyceryl distearate, forms of acrylic acids or cellulose acetates or combinations thereof.

Other Components

Pharmaceutical compositions, in some embodiments, may include one or more pharmaceutically acceptable excipients, adjuvants, diluents or carriers which are generally known in the art. "Tablet excipients" as used herein refers to customary excipients employed in manufacturing of tablets or minitablets either from granules or by direct compression technique.

Solid forms for oral administration may contain pharmaceutically acceptable binders, sweeteners, disintegrating agents, diluents, flavourings, coating agents, preservatives, lubricants and/or time delay agents or any combinations of the foregoing.

Suitable binders include, but are not limited to, gum acacia, gelatin, corn starch, gum tragacanth, sodium alginate, forms of celluloses, and forms of pyrrolidine or polyethylene glycol.

Suitable sweeteners include, but are not limited to, sucrose, lactose, glucose, aspartame or saccharine or combinations thereof.

Suitable disintegrating agents include, but are not limited to, forms of starch, forms of celluloses, forms of pyrrolidine. Suitable diluents include, but are not limited to, lactose, sorbitol, mannitol, dextrose, kaolin, forms of cellulose, forms of starch, calcium carbonate, calcium silicate or dicalcium phosphate or combinations thereof.

Suitable surfactants include, but are not limited to, sodium lauryl sulphate, poloxamer, polyethylene glycol or polysorbate or combinations thereof.

Suitable flavouring agents include, but are not limited to, peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten or combinations thereof.

Suitable preservatives include, but are not limited to, sodium benzoate, vitamin E, alpha-tocopherol, ascorbic acid, methyl paraben, propyl paraben or sodium bisulphite or combinations thereof.

Suitable lubricants include, but are not limited to, magnesium stearate, stearic acid, sodium stearyl fumarate, sodium oleate, sodium chloride or talc or combinations thereof.

Methods of Making

Some aspects of the invention relate to a method of formulating a composition for the treatment of a disorder associated with a *H. pylori* infection. In some embodiments, the method can include the steps of preparing an immediate release first dosage composition comprising at least two antibiotic agents, preparing a delayed release second dosage composition comprising at least one proton pump inhibitor, and preparing a carrier member and introducing said first and second dosage compositions.

The present pharmaceutical compositions may be prepared by means known in the art for the preparation of pharmaceutical compositions including blending, grinding, homogenising, suspending, dissolving, emulsifying, dispersing, extrusion, spheronization, compression, drying, coating, granulating including wet and dry granulation and where appropriate, mixing of the active agents together with one or more excipients, diluents, carriers and adjuvants.

In some embodiments, the first and/or the second dosage compositions can be compressed into dosage forms having small dimensions (i.e. minitablets, pellets, granules etc. . . . ). In some embodiments, the dosage forms are compressed into about 2 mm minitablets. Each dosage form may be further coated with a protective coat.

In some embodiments, the omeprazole dosage composition can be coated with an outer and an enteric coating. In some embodiments, the outer coating layer can be Opadry®. In some embodiments, the enteric coating layer can be Acryl-EZE®. After enteric coating, an additional Opadry® clear coating can be applied. This extra coating was to protect antibiotic e.g. Amoxicillin and Rifabutin interactions with the Omeprazole enteric coating layer.

In some embodiments, the rifabutin/amoxicillin dosage compositions can be coated with Opadry® clear solution.

In some embodiments, the omeprazole dosage compositions and the rifabutin/amoxicillin dosage compositions can be filled into size 00 hard gelatin capsules.

The active ingredients of the present invention are preferably formulated in a single oral dosage form containing all active pharmaceutical ingredients. The compositions of the present invention may be formulated in either solid or liquid form. It is noted that solid formulations are preferred in view of the improved stability of solid formulations as compared to liquid formulations and better patient compliance.

The present pharmaceutical compositions may be formulated in a single solid dosage form such as in the form of capsules, tablets, lozenges, pills or troches. Typically, the first and the second dosage compositions are prepared and introduced into a carrier member. In some embodiment, the carrier member may comprise a capsule. The carrier member may be made from aqueous solutions of gelling agents such as animal protein including gelatin, plant polysaccharides or their derivatives like carrageenans or modified forms of starch and cellulose.

Dosages

Some aspects of the invention provides for the use of a therapeutically effective amount of at least two antibiotics and a therapeutically effective amount of at least one proton pump inhibitor for the manufacture of a medicament for the treatment and/or prevention of recurrence of a disorder associated with *H. pylori* infection in a patient. In some embodiments, the pharmaceutical composition comprises: (1) an immediate release first dosage composition comprising of at least two antibiotics; (2) a delayed release second dosage composition comprising a proton pump inhibitor and a coating; and (3) an outer layer encapsulating the first dosage and the second dosage compositions. In some embodiments, the coating on the second dosage composition is designed to meet the two stage test dissolution profile in a basket apparatus:

(a) release of not more than 10% of the proton pump inhibitor in 120 min in an acid stage comprising 900 ml 0.1N HCl at 100 rpm; and (b) release of not less than 75% of the proton pump inhibitor in 45 min in 900 ml phosphate buffer pH 6.8 at 100 rpm following the acid stage.

Dosages of the ansamycin and the other antibiotic(s) or antimicrobial agent(s) in the methods of the invention are in accordance with their generally known and safe dosage ranges. For example, dosages for the antimicrobial agents are well known to medical practitioners, as are suitable dosages for rifabutin when it is administered for the treatment of tuberculosis or *Mycobacterium avium* complex infection. Thus, for example the immediate release first dosage composition comprising the antibiotic(s) can comprises rifabutin in the range of about 50 mg to about 2000 mg, more typically about 150 mg, and/or amoxicillin, in the range of from about 100 mg to about 5000 mg, more typically about 3000 mg. In some embodiments, the immediate release first dosage composition comprises 50 mg rifabutin. In some embodiments, the daily dosage can comprise 3000 mg amoxicillin, 35000 mg amoxicillin or higher. In some embodiments, the daily dosage can comprise 150 mg rifabutin, 200 mg rifabutin, 250 mg rifabutin, 300 mg rifabutin or higher dosage of rifabutin. For tetracycline the typical daily dosage can be in the range of from about 50 mg to about 4000 mg, to about 1500 mg. For bismuth the typical daily dosage is in the range of from about 50 mg to about 2000 mg, more typically about 300 mg. Dosages of the PPI in the composition and methods of the invention are in accordance with their generally known and safe dosage ranges. For example, the second dosage composition can comprise omeprazole in the range of from about 10 to 20 mg. 10 to 40 mg, 10 to about 250 mg, more typically about 120 mg. The compositions of the present invention comprise a PPI in an effective amount and at least one antibiotic in an effective amount to achieve a pharmacological effect or therapeutic improvement, preferably without undue adverse side effects. A therapeutic improvement includes but is not limited to: improvement or elimination of symptoms associated with infection with *H. pylori* and increasing of gastric pH, eradication of *H. pylori* as defined by a single negative UBT (13C Urea Breath Test) result, no symptoms or minimal symptoms of dyspepsia, and/or eradication of gastritis and gastric ulcers.

Methods of Treatment

Some aspects of the invention provides for a method for the treatment and/or prevention of recurrence of a disorder associated with *Helicobacter pylori* infection in a patient requiring said treatment and/or prevention.

As used herein, the term "subject" includes both human and non-human animals.

A variety of subjects are treatable according to the subject methods. In many embodiments the subjects are "mammals" or "mammalian", where these terms are used broadly to describe organisms which are within the class mammalian, including the orders carnivore (e.g., dogs and cats), rodentia (e.g., mice, guinea pigs, and rats), and primates (e.g., humans, chimpanzees, and monkeys). In many embodiments, the subjects are humans. While the present invention may be used for the treatment of a human subject, it is to be understood that the subject methods may also be carried-out on other animal subjects such as, but not limited to, mice, rats, dogs, cats, livestock and horses, etc. Accordingly, it is to be understood that any subject in need of being treated according to the subject invention is suitable.

As used herein, the term "treatment" is meant that at least an amelioration of the symptoms or risks associated with a disorder or condition (e.g. a gastrointestinal disorder associated with a *Helicobacter pylori* infection) afflicting the subject is achieved, where amelioration is used in a broad sense to refer to at least a reduction in the magnitude of a parameter, e.g., symptom or risk, associated with the condition being treated. As such, treatment also includes situations where the condition, or at least symptoms associated therewith, are completely inhibited, e.g., prevented from happening, or stopped, e.g. terminated, such that the subject no longer suffers from the condition, or at least the symptoms that characterize the condition. "Treatment" also includes the prevention of a relapse episode in a subject or should the relapse episode occur then the term "treatment" is as above. The treatment typically comprises the eradication of *Helicobacter pylori* in the subject.

In some embodiments, the method of treatment comprises administering to said patient a therapeutically effective amount of a composition comprising (1) an immediate release first dosage composition comprising of at least two antibiotics; (2) a delayed release second dosage composition comprising a proton pump inhibitor and a coating; and (3) an outer layer encapsulating the first dosage and the second dosage compositions. In some embodiments, the coating on the second dosage composition is designed to meet the two stage test dissolution profile in a basket apparatus:

(a) release of not more than 10% of the proton pump inhibitor in 120 min in an acid stage comprising 900 ml 0.1N HCl at 100 rpm; and (b) release of not less than 75% of the proton pump inhibitor in 45 min in 900 ml phosphate buffer pH 6.8 at 100 rpm following the acid stage.

In some embodiments, the outer layer encapsulating the delayed release second dosage composition and optionally the immediate release first dosage composition, the outer layer encapsulating the immediate release first dosage composition and the delayed release dosage second composition allows the release of more than 70% of the antibiotic agents in standard simulated physiological fluids within 60 minutes and allow for the delay of the release of the proton pump inhibitor in standard simulated physiological fluids by two hours and the subsequent release of more than 70% of the proton pump inhibitor in standard simulated physiological fluids within 60 minutes.

The present compositions may be administered daily. Alternatively, the present compositions can be administered twice a day. In another embodiment, the present compositions may be administered three times a day. In some embodiments, a dose comprising 50 mg rifabutin, 1000 mg amoxicillin and 40 mg omeprazole is administered three times daily. In some embodiments, the pharmaceutical composition comprises a 12.5 mg rifabutin or derivatives thereof or pharmaceutically acceptable salts or solvates thereof, 250 mg amoxicillin or derivatives thereof or pharmaceutically acceptable salts or solvates thereof and 10 mg omeprazole or derivatives thereof or pharmaceutically acceptable salts or solvates thereof.

In a further embodiment, the present compositions may be administered from the following: every 3 hours, every 4 hours, every 5 hours, every 6 hours, every 7 hours, every 8 hours, every 9 hours, every 10 hours, every 11 hours or every 12 hours. The administration of said antibiotics may be for a period of 1 week, 2 weeks, 3 weeks, 4 weeks, 5 weeks, 6 weeks, 7 weeks, 8 weeks or greater. It should be appreciated that the treatment period may continue for 3 months, 4, months, 5 months, 6 months, 7 months, 8 months, 9 months, 10 months, 11 months or 1 year or more.

In some embodiments, the present pharmaceutical compositions may be administered as follows:

TABLE 4

| Dosing Schedule | 4 capsules[1] tid. (Q8 hr) |
| --- | --- |
| Total Daily Dose | 3000 mg Amoxicillin |
|  | 120 mg Omeprazole |
|  | 150 mg Rifabutin |
| Treatment Days | 14 |

[1]Each capsule contains 250 mg amoxicillin, 10 mg omeprazole (delayed release), and 12.5 mg rifabutin In some embodiments, the pharmaceutical composition may comprise up to 3500 mg of amoxicillin and up to 300 mg rifabutin. In other embodiments, the pharmaceutical composition may comprise up to 4500 mg of amoxicillin and up to 300 mg rifabutin.

Moreover, suitable subjects for treatment according to the aspects of methods of the invention include those who have and those who have not previously been afflicted with a condition or disorder, those that have previously been determined to be at risk of suffering from a condition or disorder, and those who have been initially diagnosed or identified as being afflicted with or experiencing a condition or disorder.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLES

Example 1—Formulation of Dosage Compositions

A number of formulations comprising rifabutin, amoxicillin and omeprazole were developed and tested to compare the properties of the present composition with different formulations having the same or similar APIs.

The present formulation hereinafter comprises an outer capsule which houses at least two or more dosage compositions. The dosage compositions typically contain at least one active ingredient of the formulation. As such, one type of dosage composition includes omeprazole. Another type of dosage composition may include at least two antibiotic agents such as rifabutin or amoxicillin. In the present exemplary embodiment, rifabutin and amoxicillin are formulated together in a single dosage composition hereinafter referred to as the amoxicillin/rifabutin dosage composition. One or more amoxicillin/rifabutin dosage composition is then packaged together with one or more omeprazole dosage composition into an outer capsule. In a second exemplary embodiment, rifabutin and amoxicillin are formulated separately in a single dosage composition hereinafter referred to as the amoxicillin and rifabutin dosage composition. One or more amoxicillin dosage composition is then packaged together with one or more rifabutin dosage composition with one or more omeprazole dosage composition into an outer capsule.

Amoxicillin in the present formulation is in a high dosage relative to the other ingredients. For example, amoxicillin to rifabutin ratio can be between about 10:1 to 40:1 and amoxicillin to ratio can be between about 20:1 to about 40:1.

Initial studies to compare the present formulation with rifabutin, amoxicillin and omeprazole in a unitary tablet form found that tableting the three active pharmaceutical ingredients was not optimal due to very poor compactibility of the agents into tablet form. The high dosage of amoxicillin did not allow for the addition of further excipients to improve compactibility of the tablet. In addition, initial formulations in which the three active pharmaceutical ingredients were tableted in a single dosage form did not show omeprazole levels or only low levels of omeprazole when the omeprazole was subjected to dissolution first in an acid stage (0.1 N HCl, pH of about 1) and then in a phosphate buffer, pH6.8 (at 45 min. ramp to 200 rpm).

Furthermore, it is important in any formulation that the omeprazole is prevented from degrading in the stomach and, rather, this active ingredient should have a delayed release profile. In some embodiments, the omeprazole formulation can be designed such that once ingested, the active ingredient dissolves in the intestine rather than the stomach. However, the stability of omeprazole is a function of pH and omeprazole rapidly degrades in acid environments. Coating the omeprazole in a unitary tablet however may have the deleterious effect of delaying the release of the antibiotic agents which are required to be released immediately. In addition, as stated above, a tableted form of the three APIs showed such poor compactibility.

In contrast to the delayed release requirement of the PPI, immediate gastric release of the antibiotic agents is required in order to ensure gastric absorption. The mechanism of action of the antibiotics, in the case of *H. pylori*, is thought to be both local, at the site of infection in the gastric tissue, and systemic, including via reuptake of the antibiotics by the gastric tissue from the blood.

Preferably more than 70% of the antibiotic agents are released in T=5 to 120 minutes whereas more than 70% of the PPI (e.g. omeprazole) is released T=120 to 240 minutes in order to ensure therapeutic efficacy.

Provided herein are single formulations comprising a capsule which has the active ingredients separately compressed in individual dosage compositions. In this regard, the omeprazole dosage composition must ensure a delayed release of this active ingredient whereas the dosage composition comprising the antibiotic(s) must ensure an immediate release.

Example 2—Omeprazole Dosage Composition

Omeprazole dosage compositions were then coated with an outer and an enteric coating. The Omeprazole minitabs core formulation was coated with 1-20% Opadry® Clear, 5-50% Acryl-Eze and 1-20% Opadry® Clear.

Coating

For the outer coating, Opadry® clear solution was prepared by dissolving Opadry® powder in purified water (5% w/w). The powder was added gradually to the vortex, avoiding powder flotation on the liquid surface. This mixture was thoroughly mixed for 40-45 minutes in order to obtain a clear solution.

Acryl-EZE powder was weighed and added at 20% w/w to the center of the purified water liquid vortex in a slow steady stream, avoiding clumping and maintaining a vortex. Stirring was continued for 30 minutes. Acryl-EZE dispersion was passed through a 250 μm sieve prior to the coating process and was continuously stirred during the coating process.

During the coating process, the atomizing air pressure was 1.4-1.5 bar and the air flow was 50-100 $m^3$/h adjusted in order to obtain a good fluidization. The liquid spray rate was 5-6 g/min. The inlet temperature was between 50-55° C. and outlet temperature between 28-44° C. During enteric coating process, the inlet and outlet temperature were decreased to 32-38° C. and 25-28° C., respectively. The heating was maintained for an additional 5 minutes after both coating steps as final drying phases. After enteric coating, the additional Opadry® clear coating was applied. This extra coating was to protect the antibiotics e.g. Amoxicillin and Rifabutin interactions with the Omeprazole enteric coating layer.

In some embodiments, the proton pump inhibitor dosage composition comprises a sub-coating or inner protective layer (e.g. Opadry® clear), an enteric coating (e.g. Acryl-EZE), and a final coating or outer protective layer (e.g. Opadry® clear). In some embodiments, the sub-coating or inner protective layer was applied to protect the proton pump inhibitor from the enteric coating. In some embodiments, the final coating or outer protective layer can protect the first dosage composition (i.e. the antibiotics) from the enteric coating. The different coating can be sprayed onto the dosage composition. For example, the omeprazole dosage composition can first be sprayed with Opadry® clear until sub-coating weight gain of 10% is reached then dried. The sub-coated composition can then be sprayed with Acryl-EZE until the enteric coating weight gain of 10% is reached then dried. The enteric coated composition can then be final-coated with Opadry® clear until sub-coating weight gain of 5% is reached then dried.

Example 3—Amoxicillin Trihydrate and Rifabutin Dosage Composition Formulations Preparation of the Rifabutin/Amoxicillin Dosage Formulations The rifabutin/amoxicillin dosage cores were prepared by wet granulation and consisted of amoxicillin trihydrate, rifabutin, starch and magnesium stearate. Table 5 shows the amoxicillin/rifabutin dosage composition formulation.

TABLE 5

| Item | Description | Formula per capsule (percent by weight) |
|---|---|---|
| 1 | Amoxicillin trihydrate | 50-90% |
| 2 | Rifabutin | 1-15% |
| 3 | Pregelatinized starch, | 3-25% |
| 4 | Purified water | 10-40% |
| 5 | Magnesium stearate | 0.1-2.0% |

Compression was carried out using 2 mm punches.

Coating

In some embodiments, the rifabutin/amoxycillin dosage compositions can be coated with Opadry® clear solution in a similar process to that outlined in Example 2.

Capsules

The omeprazole dosage composition and the rifabutin/amoxycillin dosage composition were filled into hard gelatin shell capsules.

Example 4—Properties of the Pharmaceutical Composition

Amoxicillin analytical results and related substances under accelerated conditions in the present formulation of the present invention are shown in Table 6 and Table 7.

Rifabutin analytical results and related substances under accelerated conditions in the present formulation of the present invention are shown Table 8 and Table 9.

Omeprazole analytical results and related substances in the present formulation of the present invention are shown in Table 10 and Table 11 under accelerated conditions.

"Related substances" as referred herein means any variant of active pharmaceutical ingredient resulting from a molecular or chemical or physical change in the drug substance brought about during manufacture and/or storage of the dosage form by the effect of light, temperature, pH, water, or by reaction with an excipient and/or the immediate container closure system, which may or may not have deleterious effect on the safety and efficacy of the drug product.

TABLE 6

| Amoxicillin Analytical Results | | |
|---|---|---|
| Active Formulation | | Amoxicillin Minitab |
| Dose strength (Amoxicillin) | | 250 mg |
| Storage Condition | | 40° C./75% RH |
| Assay (% of nominal content) Rev.: USP limit for capsules 90-120% | T = 0 | 88.2% (n = 2: 88.4, 88.1) |

TABLE 6-continued

| Amoxicillin Analytical Results | | |
|---|---|---|
| Active Formulation | | Amoxicillin Minitab |
| Dose strength (Amoxicillin) | | 250 mg |
| Storage Condition | | 40° C./75% RH |
| Related Substances Rev.: USP Limits for API Impurity A: 0.5% Individual specified or not: 1.0% Total 5.0% | T = 0 | Total: 3.47% area Largest impurity: 0.84% area @ RRT 4.57 |
| | T = 1 month | Total: 5.08% area Largest impurity: 1.36% area @ RRT 4.57 |
| Dissolution 900 ml of water 75 rpm At 30 minutes ramped to 200 rpm (n = 2) | T = 0 | Tiime (min.) %  LC |
| | | 30 | 48 |
| | | | (58, 37, 47) |
| | | 45 | 81 |
| | | | (86, 70, 86) |
| | | Apparatus: paddles |
| Rev.: USP Limit for capsules NLT 80% Q in 60 min. at 100 RPM, Apparatus I | T = 1 month | Time (min.) | % LC |
| | | 30 | 59 |
| | | | (66, 65, 48) |
| | | 45 | 88 |
| | | | (92, 85, 87) |
| | | Apparatus: paddles |
| Content Uniformity (% of nominal content) Rev.: USP<905>Limit L1 ≤15 | T = 0 | Sample | % LC |
| | | 1 | 95.7 |
| | | 2 | 94.4 |
| | | 3 | 106.4 |
| | | 4 | 88.8 |
| | | 5 | 94.2 |
| | | 6 | 100.9 |
| | | 7 | 109.4 |
| | | 8 | 102.5 |
| | | 9 | 94.3 |
| | | 10 | 89.9 |
| | | Average | 97.7 |
| | | % RSD | 7.0 |
| | | Minimum | 88.8 |
| | | Maximum | 109.4 |
| | | AV (L1) | 17 |

TABLE 7

| Amoxicillin Related Substances | | | | |
|---|---|---|---|---|
| | Amoxicillin Minitab 250 mg | Amoxicillin API | L143-01045 Amoxicillin Minitab 250 mg | Amoxicillin API |
| | T = 0 | | T = 1 Month | |
| RRT | % area | % area | % area | % area |
| 0.24 | 0.24 | 0.25 | 0.23 | 0.24 |
| 0.27 | <0.05 | <0.05 | <0.05 | 0.02 |
| 0.31 | ND | ND | <0.05 | 0.00 |
| 0.40 | ND | ND | <0.05 | 0.01 |
| 0.47 | ND | <0.05 | <0.05 | 0.04 |
| 0.54 | 0.17 | 0.10 | 0.15 | 0.11 |
| 0.68 | <0.05 | 0.27 | 0.06 | 0.01 |
| 0.75 | 0.43 | <0.05 | 0.54 | 0.37 |
| 0.84 | <0.05 | <0.05 | <0.05 | 0.01 |
| 2.02 | <0.05 | 0.22 | <0.05 | 0.03 |
| 3.21 | 0.22 | ND | 0.17 | 0.23 |
| 3.32 | <0.05 | ND | ND | 0.02 |
| 3.47 | <0.05 | ND | 0.10 | 0.01 |
| 3.67 | 0.34 | 0.31 | 0.60 | 0.34 |
| 4.38 | 0.36 | 0.33 | 0.71 | 0.36 |
| 4.57 | 0.84 | 0.07 | 1.36 | 0.62 |
| 4.59 | ND | 0.16 | ND | ND |
| 4.95 | ND | <0.05 | ND | ND |
| 5.02 | ND | <0.05 | ND | ND |
| 5.06 | ND | <0.05 | ND | ND |
| 5.22 | ND | <0.05 | 0.15 | 0.07 |

TABLE 7-continued

Amoxicillin Related Substances

| | Amoxicillin Minitab 250 mg T = 0 | | L143-01045 Amoxicillin Minitab 250 mg T = 1 Month | |
|---|---|---|---|---|
| RRT | % area | Amoxicillin API % area | % area | Amoxicillin API % area |
| 5.56 | ND | 0.09 | 0.72 | 0.46 |
| 5.66 | 0.10 | 0.42 | 0.28 | 0.05 |
| 5.71 | 0.78 | <0.05 | 0.23 | ND |
| Total | 3.47 | 2.21 | 5.08 | 3.01 |

TABLE 8

Rifabutin Analytical Results

| Active Formulation Dose strength (Rifabutin) Storage Condition | | Rifabutin Minitab 12.5 mg 40° C./75% RH |
|---|---|---|
| Assay | T = 0 | 64.4% |
| USP Limit for capsules 90-110% | T = 1 month | (n = 2: 66.5, 62.3) 71.0% (n = 2: 73.2, 68.8) |
| Related Substances USP Limits for capsules Individual unspecified: 0.5% Individual specified: 1.0% Total 4.5% | T = 0 | Total: 1.21% area Largest impurity: 0.28% area @ RRT 0.15 |
| | T = 1 month | Total: 2.09% area Largest impurity: 0.44% area @ RRT 0.49 |
| Dissolution 900 ml of 0.01N HCl 100 rpm At 30 minutes ramped to 200 rpm (n = 2) USP Limit for capsules NLT 75%(Q) in 45 min. at 100 RPM, Apparatus I | T = 0 | Time (min.)   % LC 30   83 (85, 80, 85) Apparatus: paddles |
| | T = 1 month | Time (min.)   % LC 30   77 (71, 69, 91) Apparatus: paddles |
| Content Uniformity (% of nominal content) Rev.: USP<905>Limit L1 ≤ 15 | T = 0 | Sample   % LC 1   80.5 2   77.8 3   61.1 4   91.7 5   68.9 6   73.5 7   85.7 8   77.5 9   79.2 10   80.0 Average   77.6 % RSD   10.9 Minimum   61.1 Maximum   91.7 AV (L1)   41 |

ND = not detected
AV = Acceptance Value

TABLE 9

Rifabutin Related Substances

| | Rifabutin Minitab 12.5 mg T = 0 | | Rifabutin Minitab 12.5 mg T = 1 Month | |
|---|---|---|---|---|
| RRT | % area | Rifabutin API % area | % area | Rifabutin API % area |
| 0.17 | 0.28 | 0.02 | ND | ND |
| 0.25 | ND | ND | 0.14 | 0.05 |
| 0.48 | 0.15 | ND | 0.44 | 0.13 |
| 0.55 | ND | 0.04 | 0.21 | ND |
| 0.59 | 0.12 | 0.13 | 0.16 | 0.07 |
| 0.61 | ND | ND | 0.15 | 0.64 |
| 0.66 | ND | 0.02 | 0.05 | ND |
| 0.71 | 0.10 | 0.11 | 0.12 | ND |
| 0.75 | ND | 0.02 | ND | 0.05 |
| 0.77 | ND | 0.02 | ND | ND |
| 0.78 | ND | 0.02 | ND | ND |
| 0.80 | 0.05 | 0.06 | ND | 0.14 |
| 0.85 | ND | 0.03 | ND | 0.05 |
| 0.89 | ND | 0.02 | ND | 0.05 |
| 0.95 | 0.11 | 0.10 | 0.22 | 0.30 |
| 0.96 | 0.10 | 0.11 | 0.16 | 0.15 |
| 1.05 | ND | ND | ND | 0.09 |
| 1.12 | 0.09 | 0.09 | 0.11 | 0.13 |
| 1.17 | 0.20 | 0.25 | 0.25 | 0.16 |
| 1.21 | ND | 0.04 | 0.08 | 0.10 |
| 1.25 | ND | 0.05 | ND | ND |
| Total | 1.21 | 1.13 | 2.09 | 2.11 |

In some embodiments, an average of no less than 80% of amoxicillin is released in 60 min at 100 rpm in a baskets apparatus (900 ml 0.01 N HCl, at 100 rpm in a baskets apparatus). In some embodiments, an average of 90%, 96%, and 97% of the amoxicillin is released in an in vitro dissolution assay at 20, 30, and 45 minutes, respectively.

In some embodiments, the content uniformity of amoxicillin has an average of 102.1% LC, with a % RSD of 2.1 and with an acceptance value of 6 and an acceptance value AV (L1) of 15.

In some embodiments, an average of no less than 75% of rifabutin is released in 45 min at 100 rpm in a baskets apparatus (900 ml 0.01 N HCl, at 100 rpm in a baskets apparatus). In some embodiments, an average of 95, 97, and 98% of the rifabutin is released in an in vitro dissolution assay at 20, 30, and 45 minutes, respectively.

In some embodiments, the content uniformity of rifabutin has an average of 96.6% LC, with a % RSD of 3.0 and with an acceptance value of 9 and an acceptance value AV (L1) of 25.

TABLE 10

Omeprazole Analytical Results

| Active Formulation Dose strength (Omeprazole) Storage Condition | | Omeprazole Minitab 10 mg 40° C./75% RH |
|---|---|---|
| Assay (% of nominal content) USP Limit for capsules 90-110% | T = 0 | 89.8% (n = 2: 86.3, 93.2) |
| | T = 1 month | 84.9% (n = 2: 76.5, 93.3) |
| Related Substances USP Limits for capsules Individual specified or not: 0.5% Total 2.0%. | T = 0 | Total: 4.22% area Largest impurity: 1.98% area @ RRT 0.39 |
| | T = 1 month | Total: 4.92% area Largest impurity: 1.73% area @ RRT 0.38 |

TABLE 10-continued

Omeprazole Analytical Results

| Active Formulation Dose strength (Omeprazole) Storage Condition | | Omeprazole Minitab 10 mg 40° C./75% RH | |
|---|---|---|---|
| Dissolution USP limit for delayed - Release capsules, Test 2 Acid Stage: 900 ml 0.1N HCl, 100 rpm Apparatus I NMT 10% in 120 min, Buffer Stage: 900 ml Phosphate buffer pH 6.8, 100 rpm, Apparatus I @ 45 minutes ramp to 200 rpm NLT 75Q in 45 min | T = 0 | Time (min.) Acid Stage 120 Buffer Stage 30 45 60 | % LC No peak 82 (87, 81, 78) 82 (87, 81, 78) 81 (85, 80, 77) |
| | T = 1 month | Apparatus: baskets Time (min.) Acid Stage 120 Buffer Stage 30 45 60 Apparatus: baskets | % LC No peak 75 (92, 65, 68) 74 (92, 63, 67) 73 (91, 63, 66) |
| Content Uniformity (% of nominal content) Corealis-14301-C omeprazole Rev.: USP<905>Limit L1 ≤ 15 | T = 0 | Sample 1 2 3 4 5 6 7 8 9 10 Average % RSD Minimum Maximum AV (L1) | % LC 71.8 76.0 95.7 61.9 82.5 76.1 64.3 67.6 66.4 69.2 73.2 13.8 61.9 95.7 50 |

ND = not detected

TABLE 11

Omeprazole Related Substances

| | Omeprazole Minitab 10 mg T = 0 | Omeprazole API T = 0 | Omeprazole Minitab 10 mg T = 1 month | Omeprazole API T = 1 month |
|---|---|---|---|---|
| RRT | % area | % area | % area | % area |
| 0.39 | 1.98 | ND | 1.73 | 0.92 |
| | | | 0.51 | |
| 0.43 | 0.73 | 0.03 | 0.53 | 0.03 |
| 0.48 | 0.28 | ND | 0.31 | |
| 0.52 | 0.65 | ND | 0.66 | 0.03 |
| 0.55 | 0.08 | 0.02 | 0.18 | 0.02 |
| 0.60 | 0.16 | 0.02 | 0.21 | 0.18 |
| 0.73 | ND | <0.01 | 0.19 | |
| 0.78 | 0.05 | 0.02 | 0.10 | 0.06 |
| 0.81 | 0.05 | <0.01 | 0.22 | |
| 1.13 | 0.10 | 0.02 | 0.08 | 0.05 |
| 1.35 | 0.09 | 0.08 | | |
| 1.54 | 0.05 | 0.05 | | |
| 2.72 | | | | 0.04 |
| 3.71 | | | 0.21 | 0.39 |
| 3.74 | | | | 0.24 |
| 3.83 | | | | 0.50 |
| Total | 4.22 | 0.24 | 4.92 | 2.46 |

In some embodiments, an average of 0% of omeprazole is released in an acid stage (pH1), and 90, 90, and 86% of the omeprazole is released in an in vitro dissolution assay at 20, 30, and 45 minutes following the acid stage, respectively. In some embodiments, not more than 10% of the proton pump inhibitor is released in an acid stage (900 ml 0.1N HCl at 100 rpm, pH1), and not less than 75% of the proton pump inhibitor is released in an in vitro dissolution assay (900 ml phosphate buffer pH 6.8 at 100 rpm) at 45 minutes following the acid stage.

In some embodiments, the content uniformity of omeprazole has an average of 101.9% LC, with a % RSD of 1.9 and with an acceptance value of 5 and an acceptance value AV (L1) of 15.

Example 5—Stability of Omeprazole, Amoxicillin and Rifabutin

TABLE 12

Related Substances Omeprazole under long term conditions

| Specification | Time: 0 | | 3 months | | 6 months | |
|---|---|---|---|---|---|---|
| Omeprazole related compound F&G NMT 0.5% | No peak detected | | No peak detected | | No peak detected | |
| 5-Methoxy-1H-benzimidazole-2-thiol NMT 0.5% | 0.1% (at 0.92 RRT) | | 0.1% (at 0.92 RRT) | | 0.1% (at 0.91 RRT) | |
| Single other impurity NMT 0.5% | RRT 0.58 1.09 1.13 1.88 | % w/w 0.1 0.1 0.1 0.1 | RRT 1.09 | % w/w <0.1 | RRT 0.41 0.43 0.56 0.79 1.10 1.34 | % w/w <0.1 <0.1 <0.1 <0.1 0.1 <0.1 |
| Total impurities NMT 2.0% | 0.5% | | 0.1% | | 0.3% | |

The stability data indicated that omeprazole, amoxicillin and rifabutin are stable under standard temperature and humidity conditions. There was no decomposition of omeprazole under standard condition as is indicated in Table 12. At time, 0, 3 months, and 6 months there were no peaks detected upon analysis of the samples by HPLC corresponding to omeprazole minitab and other related impurity remained at 0.1% throughout the analysis well below 2% limit required.

Example 6—In Vivo Pharmacokinetic Study

A single center, randomized, single and multiple doses, open-label, 2-period, 2-sequence, crossover study was carried out on male and female volunteers.

A Phase I Open-Label, 2-Arm Crossover Study to Evaluate the Relative Bioavailability of the pharmaceutical composition, also herein as test formulation (Rifabutin/Amoxicillin/Omeprazole 12.5 mg/250 mg/10 mg) capsules given 3 times a day, every 8 hours, compared to the concomitant administration of the three drug substance components in fasted healthy volunteers (Table 13). Test formulation (Treatment-1) was analyzed in comparison to the pharmacokinetics of the reference drugs rifabutin, amoxicillin and omeprazole given concomitantly (Treatment-2) under fasting conditions.

Treatment-1: 4× Test formulation Amoxicillin, Rifabutin, Omeprazole 250 mg/12.5 mg/10 mg capsules (Test) given three times daily, in the morning, afternoon and evening, 8 hours apart, for a total daily oral dose of 3000 mg/150 mg/120 mg.

Treatment-2: 1× Mycobutin 150 mg capsule (Reference-1)+2× Amoxicillin 500 mg capsule (Reference-2)+1× Prilosec® 40 mg delayed-release capsule (Reference-3) taken concomitantly each given three times daily, in the morning, afternoon and evening, 8 hours apart, for a total daily oral dose of 150 mg rifabutin/3000 mg amoxicillin/120 mg omeprazole.

TABLE 13

|  | Treatment: | | | |
|---|---|---|---|---|
|  | Treatment-1 | Treatment-2 | | |
|  | Drug Code: | | | |
|  | Test | Reference-1 | Reference-2 | Reference-3 |
| Formulation: | Amoxicillin, Rifabutin, Omeprazole 250 mg/12.5 mg/10 mg capsule | Mycobutin® 150 mg capsule | Amoxicillin 500 mg capsule | Prilosec® 40 mg delayed-release capsule |
| Measured Content: | | | | |
| Amoxicillin: | 248.6 mg/capsule | — | N/AV | — |
| Rifabutin: | 12.1 mg/capsule | N/AV | — | — |
| Omeprazole: | 10.0 mg/capsule | — | — | N/AV |

Diagnosis and Main Criteria of Inclusion:

Male and female volunteers, non- or ex-smokers, of at least 18 years of age with a body mass index greater than or equal to 18.50 and below 30.00 kg/m$^2$ were included in the study. Subjects were in good health as determined by a medical history, complete physical examination (including vital signs), electrocardiogram (ECG) and the usual clinical laboratory tests (general biochemistry (including bicarbonate), hematology, urinalysis) including negative Human Immunodeficiency Virus (HIV), Hepatitis B and Hepatitis C tests as well as negative screening of alcohol and drugs of abuse in urine and negative beta Human Chorionic Gonadotropin (HCG) qualitative serum pregnancy test (for female subjects). Genotyping for the CYP 2C19 gene was also performed.

Number of Subjects (Planned and Analyzed):
Planned for inclusion: 16
Included: 16
Drop-out: 1
Analyzed: 15
Considered in the pharmacokinetic and statistical analysis of:
Rifabutin and 25-O-desacetyl-rifabutin: 15 (Subject #016 was included in the analysis of $C_{max}$, $T_{max}$, $C_{24}$ and $AUC_{0-24}$ only)
Amoxicillin: 15
Omperazole: 15
Considered in the safety analysis: 16
Test Product, Dose and Mode of Administration
Dosage form/Route of administration: Capsule/Oral
Regimen: Single dose of 4×12.5 mg rifabutin/250 mg amoxicillin/10 mg omeprazole given three times daily, in the morning, afternoon and evening, 8 hours apart, for a total daily oral dose of 150 mg rifabutin/3000 mg amoxicillin/120 mg omeprazole.

Reference-1 Product, Dose and Mode of Administration:
Name: Mycobutin®
Dosage form/Route of administration: Capsule/Oral
Regimen: Single 150 mg dose (1×150 mg) given once in the morning, for a total daily oral dose of 150 mg.
Reference-2 Product, Dose and Mode of Administration:
Name: Amoxicillin
Dosage form/Route of administration: Capsule/Oral
Regimen: Single 1000 mg dose (2×500 mg) given three times daily, in the morning, afternoon and evening, 8 hours apart, for a total of a total daily oral dose of 3000 mg.
Reference-3 Product, Dose and Mode of Administration:
Name: Prilosec®
Dosage form/Route of administration: Delayed Release Capsule/Oral
Regimen: Single 40 mg dose (1×40 mg), given three times daily, in the morning, afternoon and evening, 8 hours apart, for a total of a total daily oral dose of 120 mg
Treatments:
Treatment-1:
4 capsules of the Test formulation was given three times daily, in the morning, afternoon and evening, 8 hours apart, for a total daily oral dose of 150 mg rifabutin/3000 mg amoxicillin/120 mg omeprazole)
Treatment-2:
Reference-1 drug (Rifabutin) was given once in the morning together with 2 capsules of Reference-2 drug (amoxicillin) and 1 capsule of Reference-3 drug (Omeprazole). Each reference drug was given three times daily, in the morning, afternoon and evening, 8 hours apart, for a total daily oral dose of 150 mg rifabutin/3000 mg amoxicillin/120 mg omeprazole).
Duration of Treatment:
Single and multiple oral doses were administered under fasting conditions in each study period. The drug administrations were separated by a wash-out of 14 calendar days.
Blood Sampling Points:
For each Treatment in each study period, 78 blood samples were collected on 26 occasions. The first blood sample was collected prior to the first (morning) drug administration while the others were collected 0.5, 1, 2, 3, 4, 6, 8 (Pre-2$^{nd}$ dose in the afternoon), 8.5, 9, 10, 11, 12, 14, 16 (Pre-3$^{rd}$ dose in the evening), 16.5, 17, 18, 19, 20, 22, 24, 32, 48, 56 and 72 hours after the morning administration.
Criteria for Evaluation
Analytical Methods:
Rifabutin, 25-O-desacetylrifabutin, amoxicillin and omeprazole human plasma concentrations were measured by HPLC with MS/MS detection.

Assay ranges were as follows:
Rifabutin: 2.00 ng/mL to 800.00 ng/mL
25-O-desacetylrifabutin: 0.200 ng/mL to 100.000 ng/mL
Amoxicillin: 0.200m/mL to 40.000m/mL
Omeprazole: 5.00 ng/mL to 2500.00 ng/mL
Safety:

Safety was evaluated through assessment of adverse events and standard laboratory evaluations.

Mathematical Model and Statistical Methods of Pharmacokinetic Parameters

The pharmacokinetics of rifabutin, 25-O-desacetylrifabutin, amoxicillin and omeprazole were to be evaluated. Main absorption and disposition parameters using a non-compartmental approach with a log-linear terminal phase assumption. Trapezoidal rule to estimate the area under the curve. The pharmacokinetic parameters for this study were to be $C_{max}$, $T_{max}$, $C_{min}$, $C_{24}$, $C_{last}$, $T_{last}$, $AUC_{0-24}$, $AUC_{\infty}$, $K_{el}$ and $T_{1/2el}$.

Statistical analysis of $T_{max}$ based on a non-parametric approach. Statistical analysis of all other pharmacokinetic parameters based on a parametric ANOVA model. Two-sided 90% confidence interval of the ratio of geometric LSmeans obtained from the ln-transformed pharmacokinetic parameters.

$C_{min}$: Minimum observed plasma concentration after the first (morning) drug administration (in ng/ml)

$C_{max}$: Maximum observed plasma concentration (in ng/ml)

$C_{24}$: Observed plasma concentration at 24 hours (in ng/ml)

$C_{last}$: Last observed quantifiable plasma concentration (in ng/ml)

$T_{max}$: Time of maximum observed plasma concentration; if it occurs at more than one time point, $T_{max}$ is defined as the first time point with this value (in hours)

$T_{last}$: Time of last observed plasma concentration (in hours)

$T_{LQC}$: Time of last observed quantifiable plasma concentration (in hours)

$AUC_{24}$ ($AUC_{0-24}$); Cumulative area under the plasma concentration time curve calculated from 0 to $T_{LQC}$ (in ng·h/ml)

$AUC_{\infty}$ ($AUC_{0-\infty}$): Area under the plasma concentration time curve extrapolated to infinity, calculated as $AUC_T + \hat{C}_{LQC}/\lambda_z$, where $\hat{C}_{LQC}$ is the estimated concentration at time $T_{LQC}$ in ng·h/ml)

$T_{LIN}$: Time point where log-linear elimination phase begins $K_{el}(\lambda_z)$: Apparent elimination rate constant, estimated by linear regression of the terminal linear portion of the log concentration versus time curve (in $h^{-1}$)

$T_{1/2el}(T_{half})$: Terminal elimination half-life, calculated as $\ln(2)/\lambda_z$ (in hours).

ANOVA Model:
  fixed factors: sequence, period, treatment
  random factor: subject (nested within sequence)
Safety:
  Descriptive statistics.
Pharmacokinetic Results:

A single center, randomized, single and multiple doses, open-label, two-way, crossover comparative bioavailability study was conducted under fasting conditions on 16 healthy male and female subjects. The rate and extent of absorption of rifabutin, 25-O-desacetylrifabutin, amoxicillin and omeprazole were measured and compared following the administration of the fixed combination Test formulation (Treatment-1; 4 capsules, given three times daily, in the morning, afternoon and evening, 8 hours apart) in comparison to the pharmacokinetics of rifabutin (Reference-1), amoxicillin (Reference-2) and omeprazole (Reference-3) given concomitantly (Treatment-2; Reference-1 given once in the morning+2 capsules of Reference-2 and 1 capsule of Reference-3 each given three times daily, in the morning, afternoon and evening, 8 hours apart). Among the four analytes examined, only the relative bioavailability of amoxicillin in the two formulations was equivalent under fasting conditions. The results from measured data based on 15 subjects are presented in the following summary tables.

Safety Results:

Seven (7) (43.8%) of the 16 subjects included in this study experienced a total of 11 adverse events.

Three (3) subjects (18.8%) reported 4 adverse events (3 different System Organ Classes and 4 different Preferred Terms) following the administration of the test formulation tid and 6 subjects (40.0%) reported 7 adverse events (4 different System Organ Classes and 4 different Preferred Terms) following the administration of Mycobutin qd+Amoxicillin tid+Prilosec tid.

The adverse events reported during this study were all of mild severity. No moderate or severe adverse events were observed during the study.

No serious adverse events or deaths were reported during this study.

No adverse events required the use of medications following the first dosing.

One (1) subject (6.3%) was withdrawn from the study for safety reasons:

Subject #007 was withdrawn by the physician before dosing of period 2 following the adverse events alanine aminotransferase increased and aspartate aminotransferase increased of mild intensities.

Results

Figure 1:
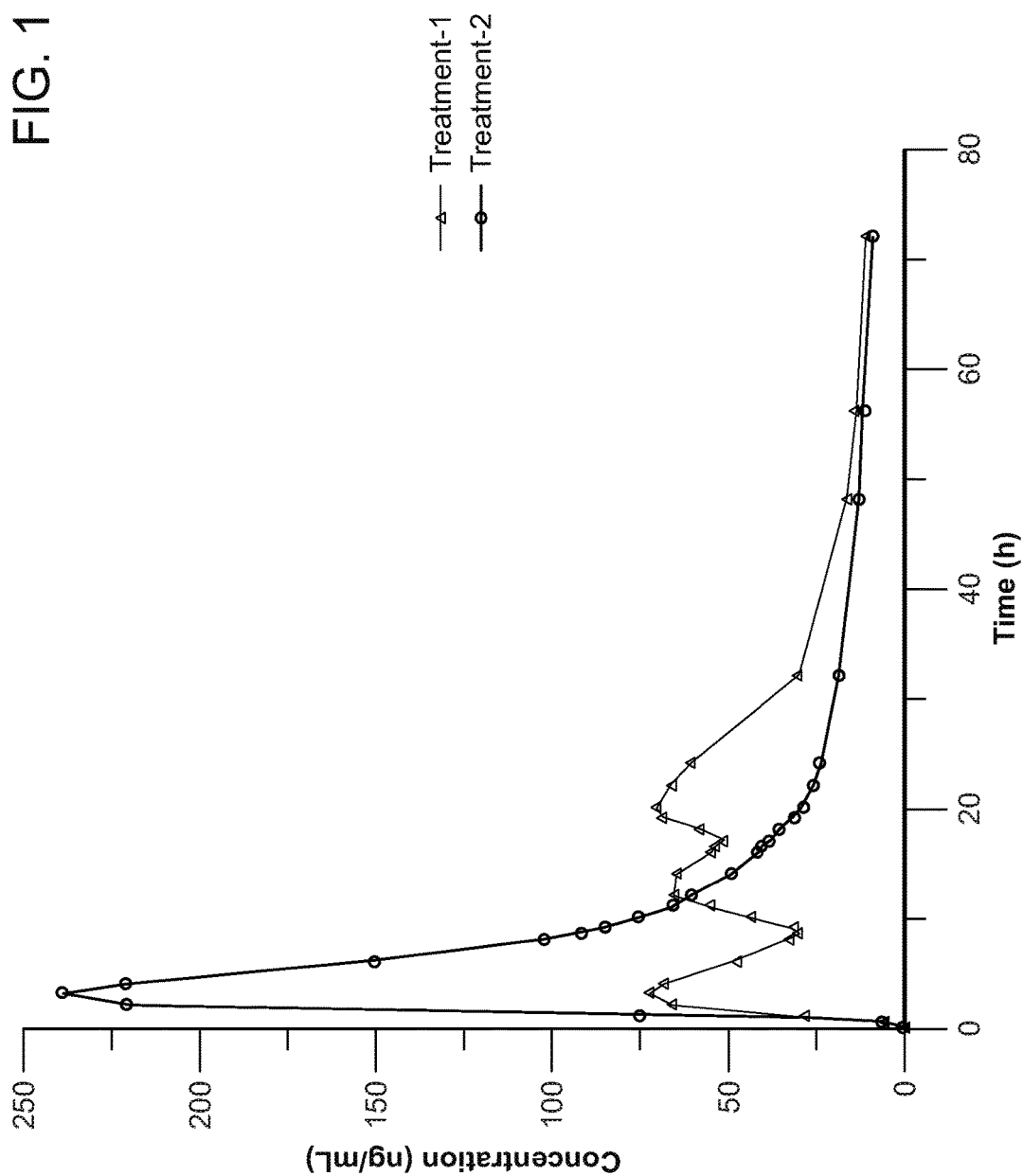
FIG. 1 illustrates the linear profile of the mean for rifabutin in treatment 1 using the test formulation of the present disclosure and treatment 2 using the concomitant administration of the three API according to some embodiments. Treatment 1 corresponds to the administration of a 4 capsule of a single dose comprising 12.5 mg rifabutin/250 mg amoxicillin/10 mg omeprazole given three times daily, in the morning, afternoon and evening, 8 hours apart, for a total daily oral dose of 150 mg rifabutin/3000 mg amoxicillin/120 mg omeprazole. Treatment 2 corresponds to the concomitant administration of rifabutin, amoxicillin and omeprazole for a total daily oral dose of 150 mg rifabutin/3000 mg amoxicillin/120 mg omeprazole. In Treatment 2, 150 mg of rifabutin was given once in the morning. Two capsules of amoxicillin 500 mg amoxicillin and one capsule of 40 mg omeprazole were given three times daily, in the morning, afternoon and evening, 8 hours apart.

Pharmacokinetics parameters results for rifabutin are shown in Table 14 and Table 15. FIG. 1 shows the linear profile of the mean for rifabutin in treatment 1 using the test formulation of the present disclosure and treatment 2 using the concomitant administration of the three API according to some embodiments. FIG. 2 shows the logarithmic profile of the mean for rifabutin in treatment 1 using the test formulation of the present disclosure and treatment 2 using the concomitant administration of the three API according to some embodiments.

TABLE 14

Summary of Pharmacokinetic Parameters results-
Rifabutin- Test vs. Reference

| Parameter | TEST tid | | REFERENCE Mycobutin qd + Amoxicillin tid + Prilosec tid | |
|---|---|---|---|---|
| | Mean | C.V. (%) | Mean | C.V. (%) |
| $C_{max}$ (ng/mL) | 87.58 | 24.3 | 247.64 | 32.6 |
| ln ($C_{max}$) | 4.4467 | 5.2 | 5.4553 | 6.7 |
| $C_{min}$ | 4.23 | 87.7 | 4.28 | 84.0 |
| ln ($C_{min}$) | 1.6602 | 31.8 | 1.8628 | 14.9 |
| $C_{24}$ (ng/mL) | 60.58 | 30.4 | 23.57 | 32.7 |
| ln ($C_{24}$) | 4.0579 | 7.9 | 3.1039 | 11.6 |
| $C_{last}$ (ng/mL) | 9.84 | 39.4 | 8.70 | 44.6 |
| ln ($C_{last}$) | 2.2100 | 18.7 | 2.0607 | 23.5 |
| $T_{max}$ (hours)* | 16.50 | 41.3 | 3.00 | 20.3 |
| $T_{last}$ (hours)* | 72.00 | 0.0 | 72.00 | 0.5 |
| $AUC_{0-24}$ (ng · h/mL) | 1323.84 | 23.2 | 1999.25 | 27.4 |
| ln ($AUC_{0-24}$) | 7.1646 | 3.1 | 7.5579 | 4.3 |

TABLE 14-continued

Summary of Pharmacokinetic Parameters results-
Rifabutin- Test vs. Reference

| | TEST tid | | REFERENCE Mycobutin qd + Amoxicillin tid + Prilosec tid | |
|---|---|---|---|---|
| Parameter | Mean | C.V. (%) | Mean | C.V. (%) |
| $AUC_{0-\infty}$ (ng · h/mL) | 2734.95 | 27.9 | 3184.56 | 34.7 |
| ln ($AUC_{0-\infty}$) | 7.8775 | 3.6 | 8.0049 | 4.7 |
| $\lambda_Z$ (hours$^{-1}$) | 0.0257 | 29.7 | 0.0194 | 31.2 |
| $T_{half}$ (hours) | 29.10 | 26.9 | 39.33 | 32.3 |

*median is presented

TABLE 15

Rifabutin

| | | Geometric LSMeans* | | | | |
|---|---|---|---|---|---|---|
| | Intra-Subject C.V. | | REFERENCE Mycobutin qd + Amoxicillin tid + | Ratio | 90% Confidence Limits (%) | |
| Parameter | (%) | TEST tid | Prilosec tid | (%) | Lower | Upper |
| $C_{max}$ | 20.9 | 85.03 | 234.48 | 36.26 | 31.72 | 41.46 |
| $C_{min}$ | 44.5 | 5.27 | 6.44 | 81.80 | 57.01 | 117.37 |
| $C_{24}$ | 17.7 | 57.44 | 22.30 | 257.60 | 229.95 | 288.58 |
| $C_{last}$ | 17.9 | 9.12 | 7.85 | 116.10 | 103.01 | 130.85 |
| $AUC_{0-24}$ | 16.4 | 1289.39 | 1919.26 | 67.18 | 60.44 | 74.68 |
| $AUC_{0-\infty}$ | 15.3 | 2637.37 | 2995.46 | 88.05 | 79.46 | 97.56 |

*units are ng/mL for $C_{max}$, $C_{min}$, $C_{24}$, $C_{last}$ and ng · h/ml for $AUC_{0-24}$ and $AUC_{0-\infty}$ In some aspects of the invention, the pharmaceutical composition, comprises: (1) an immediate release first dosage composition comprising a first antibiotic and at least a second antibiotic wherein the first antibiotic is rifabutin or derivatives thereof and pharmaceutically acceptable salts and solvates thereof, wherein the first dosage core comprises 12.5 mg rifabutin and provides, when administered at a dose of 50 mg three times a day to a human in a fasted state an in vivo plasma profile having (a) a mean $C_{max}$ of 87 ng/ml; (b) a Geometric LSMeans of 85 ng/ml; (c) a mean $AUC_{0-24}$ of 1320 ng·h/ml; and (c) a mean T max of 16.50 h based on a three times a day dose administration; (2) a delayed release second dosage composition comprising a proton pump inhibitor and a coating; and (3) an outer layer encapsulating the first dosage composition and the second dosage composition.

In some aspects of the invention, the pharmaceutical composition, comprises: (1) an immediate release first dosage composition comprising a first antibiotic and at least a second antibiotic wherein the first antibiotic is rifabutin or derivatives thereof and pharmaceutically acceptable salts and solvates thereof, wherein the first dosage core comprises 12.5 mg rifabutin and provides, when administered at a dose of 50 mg three times a day to a human in a fasted state an in vivo plasma profile having (a) a mean $C_{max}$ ranging from 60 ng/ml to 113 ng/ml; (b) a Geometric LSMeans ranging from 55 ng/ml to 110 ng/ml; (c) a mean $AUC_{0-24}$ ranging from 800 ng·h/ml to 1850 ng·h/ml; and (c) a mean T max ranging from 14 h to 19 h based on a three times a day dose administration; (2) a delayed release second dosage composition comprising a proton pump inhibitor and a coating; and (3) an outer layer encapsulating the first dosage composition and the second dosage composition.

In some aspects of the invention, the pharmaceutical composition, comprises: (1) an immediate release first dosage composition comprising a first antibiotic and at least a second antibiotic wherein the first antibiotic is rifabutin or derivatives thereof and pharmaceutically acceptable salts and solvates thereof, wherein the first dosage core comprises 12.5 mg rifabutin and provides, when administered at a dose of 50 mg three times a day to a human in a fasted state an in vivo plasma profile having (a) a $C_{max}$ to $C_{min}$ ratio of less than 57.8; and (b) a mean T max of 16.50 h based on a three times a day dose administration; (2) a delayed release second dosage composition comprising a proton pump inhibitor and a coating; and (3) an outer layer encapsulating the first dosage composition and the second dosage composition.

Pharmacokinetics parameters results for 25-O-Desacetyl-rifabutin are shown in Table 16 and in Table 17.

TABLE 16

Summary of Pharmacokinetic Parameters results- 25-O-Desacetylrifabutin-Test vs. Reference

| | TEST tid | | REFERENCE (Mycobutin qd + Amoxicillin tid + Prilosec tid) | |
|---|---|---|---|---|
| Parameter | Mean | C.V. (%) | Mean | C.V. (%) |
| $C_{max}$ (ng/mL) | 7.469 | 24.2 | 23.350 | 36.3 |
| ln ($C_{max}$) | 1.9823 | 12.6 | 3.0866 | 12.2 |
| $C_{min}$ | 0.171 | 125.3 | 0.158 | 119.4 |
| ln ($C_{min}$) | −1.0789 | −39.2 | −1.1209 | −25.3 |
| $C_{24}$ (ng/mL) | 5.470 | 37.1 | 2.673 | 53.6 |
| ln ($C_{24}$) | 1.6289 | 24.7 | 0.8642 | 57.6 |
| $C_{last}$ (ng/mL) | 0.759 | 48.1 | 0.703 | 56.8 |
| ln ($C_{last}$) | −0.3910 | −129.9 | −0.5054 | −115.1 |
| $T_{max}$ (hours)* | 4.00 | 85.4 | 3.03 | 14.8 |
| $T_{last}$ (hours)* | 72.00 | 0.0 | 72.00 | 0.5 |
| $AUC_{0-24}$ (ng · h/mL) | 117.449 | 28.0 | 200.653 | 40.1 |
| ln ($AUC_{0-24}$) | 4.7273 | 6.2 | 5.2215 | 8.2 |
| $AUC_{0-\infty}$ (ng · h/mL) | 244.043 | 32.8 | 299.347 | 45.7 |
| ln ($AUC_{0-\infty}$) | 5.4436 | 6.4 | 5.6015 | 8.5 |
| $\lambda_Z$ (hours$^{-1}$) | 0.0286 | 46.3 | 0.0283 | 36.4 |
| $T_{half}$ (hours) | 30.79 | 65.5 | 28.08 | 41.7 |

*median is presented

TABLE 17

25-O-Desacetylrifabutin

| | | Geometric LSMeans* | | | | |
|---|---|---|---|---|---|---|
| | Intra-Subject | | REFERENCE Mycobutin qd + Amoxicillin tid + | | 90% Confidence Limits (%) | |
| Parameter | C.V. (%) | TEST tid | Prilosec tid | Ratio (%) | Lower | Upper |
| $C_{max}$ | 20.4 | 7.275 | 22.090 | 32.93 | 28.90 | 37.53 |
| $C_{min}$ | 13.1 | 0.340 | 0.308 | 110.62 | 85.53 | 143.07 |
| $C_{24}$ | 21.9 | 5.098 | 2.385 | 213.77 | 185.82 | 245.93 |
| $C_{last}$ | 20.4 | 0.673 | 0.605 | 111.15 | 97.51 | 126.70 |
| $AUC_{0-24}$ | 19.0 | 113.493 | 186.627 | 60.81 | 53.81 | 68.73 |
| $AUC_{0-\infty}$ | 18.6 | 231.271 | 270.837 | 85.39 | 75.39 | 96.72 |

*units are ng/mL for $C_{max}$, $C_{min}$, $C_{24}$, $C_{last}$ and ng · h/mL for $AUC_{0-24}$ and $AUC_{0-\infty}$ Pharmacokinetics parameters results for amoxicillin are shown in Table 18 and Table 19. FIG. 3 shows the linear profile of the mean for amoxicillin in treatment 1 using the test formulation of the present disclosure and treatment 2 using the concomitant administration of the three API according to some embodiments. FIG. 4 shows the logarithmic profile of the mean for amoxicillin in treatment 1 using the test formulation of the present disclosure and treatment 2 using the concomitant administration of the three API according to some embodiments.

TABLE 18

Summary of Pharmacokinetic Parameters results - Amoxicillin - Test vs. Reference

| | TEST tid | | REFERENCE Mycobutin qd + Amoxicillin tid + Prilosec tid | |
|---|---|---|---|---|
| Parameter | Mean | C.V. (%) | Mean | C.V. (%) |
| $C_{max}$ (µg/mL) | 15.855 | 21.1 | 15.005 | 27.0 |
| ln ($C_{max}$) | 2.7415 | 8.1 | 2.6749 | 10.0 |
| $C_{24}$ (µg/mL) | 3.711 | 68.6 | 2.737 | 56.2 |

TABLE 18-continued

Summary of Pharmacokinetic Parameters results - Amoxicillin - Test vs. Reference

| | TEST tid | | REFERENCE Mycobutin qd + Amoxicillin tid + Prilosec tid | |
|---|---|---|---|---|
| Parameter | Mean | C.V. (%) | Mean | C.V. (%) |
| ln ($C_{24}$) | 1.0798 | 67.9 | 0.8363 | 76.9 |
| $C_{last}$ (µg/mL) | 3.101 | 66.8 | 2.201 | 56.2 |
| ln ($C_{last}$) | 0.8838 | 88.7 | 0.5978 | 117.2 |
| $T_{max}$ (hours)* | 2.00 | 115.1 | 2.00 | 99.0 |
| $T_{last}$ (hours)* | 24.00 | 8.4 | 24.00 | 11.2 |
| $AUC_{0-24}$ (µg · h/mL) | 145.788 | 20.5 | 137.610 | 22.5 |
| ln ($AUC_{0-24}$) | 4.9633 | 4.0 | 4.9003 | 4.7 |
| $AUC_{0-\infty}$ (µg · h/mL) | 167.144 | 26.9 | 149.455 | 23.1 |
| ln ($AUC_{0-\infty}$) | 5.0876 | 5.0 | 4.9801 | 5.0 |
| $\lambda_Z$ (hours$^{-1}$) | 0.3132 | 44.3 | 0.3451 | 43.5 |
| $T_{half}$ (hours) | 2.96 | 77.4 | 2.40 | 47.8 |

*median is presented

TABLE 19

Amoxicillin

| | | Geometric LSMeans* | | | | |
|---|---|---|---|---|---|---|
| | Intra-Subject | | REFERENCE Mycobutin qd + Amoxicillin tid + | | 90% Confidence Limits (%) | |
| Parameter | C.V. (%) | TEST tid | Prilosec tid | Ratio (%) | Lower | Upper |
| $C_{max}$ | 12.3 | 15.545 | 14.472 | 107.41 | 99.22 | 116.29 |
| $C_{24}$ | 44.5 | 2.905 | 2.281 | 127.33 | 96.68 | 167.72 |
| $C_{last}$ | 51.0 | 2.355 | 1.780 | 132.33 | 96.91 | 180.70 |
| $AUC_{0-24}$ | 6.0 | 142.931 | 134.250 | 106.47 | 102.42 | 110.68 |
| $AUC_{0-\infty}$ | 9.1 | 161.456 | 145.287 | 111.13 | 104.75 | 117.89 |

*units are µg/mL for $C_{max}$, $C_{24}$, $C_{last}$ and µg · h/ml for $AUC_{0-24}$ and $AUC_{0-\infty}$ Pharmacokinetics parameters results for omeprazole are shown in Table 20 and Table 21. FIG. 5 shows the linear profile of the mean for omeprazole in treatment 1 using the test formulation of the present disclosure and treatment 2 using the concomitant administration of the three API according to some embodiments. FIG. 6 shows the logarithmic profile of the mean for omeprazole in treatment 1 using the test formulation of the present disclosure and treatment 2 using the concomitant administration of the three API according to some embodiments.

TABLE 20

Summary of Pharmacokinetic Parameters results - Omeprazole - Test vs. Reference

| Parameter | TEST tid | | REFERENCE Mycobutin qd + Amoxicillin tid + Prilosec tid | |
|---|---|---|---|---|
| | Mean | C.V. (%) | Mean | C.V. (%) |
| $C_{max}$ (µg/mL) | 1280.92 | 40.5 | 1294.99 | 27.5 |
| ln ($C_{max}$) | 7.0647 | 6.7 | 7.1291 | 4.0 |
| $C_{24}$ (µg/mL) | 89.01 | 69.6 | 129.11 | 76.6 |
| ln ($C_{24}$) | 4.1788 | 22.7 | 4.5537 | 23.5 |
| $C_{last}$ (µg/mL) | 89.01 | 69.6 | 80.98 | 103.2 |
| ln ($C_{last}$) | 4.1788 | 22.7 | 3.6551 | 38.8 |
| $T_{max}$ (hours)* | 2.00 | 105.3 | 12.00 | 55.4 |
| $T_{last}$ (hours)* | 24.00 | 0.1 | 24.00 | 30.0 |
| $AUC_{0-24}$ (µg · h/mL) | 7161.15 | 49.3 | 10128.37 | 36.0 |
| ln ($AUC_{0-24}$) | 8.7449 | 6.4 | 9.1587 | 4.1 |
| $AUC_{0-\infty}$ (µg · h/mL) | 7718.73 | 46.1 | 10964.00 | 33.8 |
| ln ($AUC_{0-\infty}$) | 8.8382 | 5.9 | 9.2449 | 3.9 |
| $\lambda_Z$ (hours$^{-1}$) | 0.4820 | 20.7 | 0.4151 | 34.4 |
| $T_{half}$ (hours) | 1.49 | 19.6 | 2.10 | 72.1 |

*median is presented

TABLE 21

| Omeprazole | | | | | | |
|---|---|---|---|---|---|---|
| | | Geometric LSMeans* | | | | |
| | Intra-Subject | | REFERENCE Mycobutin qd + Amoxicillin tid + | Ratio | 90% Confidence Limits (%) | |
| Parameter | C.V. (%) | TEST tid | Prilosec tid | (%) | Lower | Upper |
| $C_{max}$ | 31.7 | 1174.85 | 1243.98 | 94.44 | 77.28 | 115.41 |
| $C_{24}$ | 77.5 | 66.72 | 90.86 | 73.43 | 46.33 | 116.39 |
| $C_{last}$ | 136.2 | 66.72 | 37.24 | 179.15 | 92.23 | 347.95 |
| $AUC_{0-24}$ | 23.6 | 6344.13 | 9478.27 | 66.93 | 57.57 | 77.82 |
| $AUC_{0-\infty}$ | 21.7 | 7143.42 | 10395.80 | 68.71 | 59.39 | 79.50 |

*units are ng/mL for $C_{max}$, $C_{24}$, $C_{last}$ and ng · h/ml for $AUC_{0-24}$ and $AUC_{0-\infty}$ Conclusions:

Rifabutin and 25-O-desacetylrifabutin

The mean of the minimum observed concentrations and last observable concentrations for rifabutin and 25-O-desacetylrifabutin were similar for both treatments. Despite the 150 mg dose of rifabutin administered over 24 hours for both treatments, the extent of absorption of rifabutin was 1.5 times higher when administered as a single 150 mg capsule than as part of the test formulation tid formulation and the mean rifabutin and 25-O-desacetylrifabutin concentrations at 24 hours following the test formulation tid administration was more than double than the concentrations of rifabutin and 25-O-desacetylrifabutin observed after the Reference formulations given concomitantly. Given the study design and dosing regimen, a ⅓$^{rd}$ ratio of geometric LSmeans for the $C_{max}$ and a faster rate of absorption between the test formulation tid and mycobutin qd+amoxicillin tid+prilosec tid was anticipated.

The results presented herein show that the relative bioavailability between the test formulation tid and the Reference formulations given concomitantly (mycobutin qd+amoxicillin tid+prilosec tid) were not comparable. For both rifabutin and its metabolite, the test formulation tid to Mycobutin qd+amoxicillin tid+prilosec tid ratio of geometric LSmeans and corresponding 90% confidence interval for the $C_{max}$, $AUC_{0-24}$ and $AUC_{0-\infty}$ were all outside of the pre-specified range of 80.00 to 125.00%. For rifabutin, the ratio of Cmax to Cmin was 20.70 for the test formulation tid as compared to 57.86 for the Mycobutin qd+amoxicillin tid+prilosec tid.

Amoxicillin

Although the mean last observable plasma concentrations and those observed at 24 hours were slightly elevated for the test formulation tid in comparison to amoxicillin when given concomitantly with the reference products, the rate an extent of absorption of amoxicillin were comparable (FIGS. 3-4).

The results presented herein show that the relative bioavailability between the test formulation tid and the Reference formulations given concomitantly (mycobutin qd+amoxicillin tid+prilosec tid) were comparable for amoxicillin. The test formulation tid to Mycobutin qd+amoxicillin tid+prilosec tid ratio of geometric LSmeans and corresponding 90% confidence interval for the $C_{max}$, $AUC_{0-24}$ and $AUC_{0-\infty}$ were all within pre-specified range of 80.00 to 125.00%.

Omeprazole

Although the mean omeprazole $C_{max}$'s are similar for both treatments, the overall rate and extent of absorption are not. The results presented herein show that the relative bioavailability between the test formulation tid and the Reference formulations given concomitantly (mycobutin qd+amoxicillin tid+prilosec tid) were not comparable for omeprazole. The test formulation tid to Mycobutin qd+amoxicillin tid+Prilosec tid ratio of geometric LSmeans and corresponding 90% upper confidence limit for the $C_{max}$ were within pre-specified range of 80.00 to 125.00%, however the 90% lower confidence limit for the $C_{max}$ and the ratio of geometric LSmeans and corresponding 90% confidence interval for the $AUC_{0-24}$ and $AUC_{0-\infty}$ were all outside of the pre-specified range.

Therefore, the fixed combination Test formulation (Rifabutin/Amoxicillin/Omeprazole 12.5/250/10 mg) capsules, is judged not to have comparable bioavailability when the Reference formulations are administered concomitantly (Mycobutin® 150 mg capsule, Pharmacia & Upjohn Company, USA division of Pfizer Inc, USA+Amoxicillin 500 mg capsule, Teva Canada Limited, Canada+Prilosec® 40 mg delayed-release capsule, Merck Sharp & Dohme Corp., a subsidiary of Merck & Co., Inc USA) under fasting conditions.

The secondary objective was to assess the safety of the combination formulation on healthy volunteers. All of the 11 adverse events reported during the study were mild in severity. Less subjects receiving the test formulation experienced at least one adverse event when compared to the Reference formulations given concomitantly. No serious adverse events or deaths were reported during this study. One (1) subject (6.3%) was withdrawn from the study for safety reasons (Investigator's decision) after the administration of the test formulation tid. Overall, both treatments were generally safe and well tolerated by the subjects included in this study.

It should be noted that the $C_{max}$ of rifabutin when given at 50 mg pulsed dose three times a day has an initial lower $C_{max}$ than rifabutin when given in a single 150 mg daily dose, and therefore a superior safety profile. Rifabutin adverse effects are well known and need to be given to patients with HIV at a lower dosage due to its side effects. The pulsed dosage of 50 mg every 8 hours can avoid high Cmax in patients' plasma and as a result can lead to a better safety and pharmacokinetic profile. Additionally, the 50 mg pulsed dosage has a more consistent AUC for 48 hours and a higher Cmin at 48 hours (Treatment 1, FIG. 2) which is advantageous when compared to a single 150 mg dosage given in a concomitant administration of the API separately (Treatment 2, FIG. 2).

In some embodiments, rifabutin given in 50 mg pulsed dose three times a day can extend the length of the post-antibiotic effect (PAE) compared to a single 150 mg dose. This effect can be advantageous for eradication of intracellular bacteria that are dormant and that can become active after the termination of the therapy. The extended post-antibiotic effect can eradicate the remaining pool of the dormant bacteria. This long-acting intracellular anti-bacterial activity may ex plain the clinical efficacy of rifabutin intracellularly. In some embodiments, the activity of rifabutin when given in daily 50 mg pulsed doses can be related to its post antibiotic effect.

Example 7: Clinical Study

A randomized, double-blind, placebo-controlled study of test formulation is carried out in adult subjects complaining of epigastric discomfort that have been screened and found to be positive for *H. pylori* infection via $^{13}$C UBT and also by fecal antigen test. The placebo arm is not expected to provide any relevant comparative effectiveness measure, as the effectiveness of placebo on *H. pylori* eradication is known to approximate 0% (FDA Guidance to Industry on *H. pylori*—2009). The placebo arm is intended to provide a comparative safety measure only.

The study is conducted at up to 12 sites. Once informed consent has been obtained and upon positive screening and enrolment into the study, eligible subjects are randomized in a ratio of 1:2 between a placebo arm (n=30) and the active arm (test formulation) (n=60) Subjects receive test formulation for 14 consecutive days. Eradication of *H. pylori* infection is determined based on $^{13}$C UBT testing conducted between 28 to 35 days after completion of therapy.

Subjects are unblinded upon completion of the $^{13}$C UBT analysis.

Eradication failures ($^{13}$C UBT-positive) in the active study drug arm will undergo upper endoscopy with sampling for culture and sensitivity testing (to rifabutin, amoxicillin, clarithromycin, and metronidazole).

The test formulation and the placebo capsules in the present study have both been formulated to be identical in appearance.

Efficacy Evaluations
13C Urea Breath Test

The $^{13}$C UBT (BreathTek®, Otsuka America Pharmaceutical Inc.) is conducted at screening, and follow up visits (visit 4 and visit 8) if applicable. This is used to verify H. *Pylori* status prior to test formulation administration and to determine if *H. pylori* has been successfully eradicated. Subjects are asked to fast from solid food for at least 1 hour prior to their visit. They must not have had any antibiotics for 4 weeks prior to screening and since end of treatment, or proton pump inhibitors or bismuth preparations in the 2 weeks prior to post treatment assessment or H2 receptor antagonists the night before $^{13}$C UBT). Step-by-step procedures are presented in the BreathTek® Package Insert (provided in the laboratory manual).

Endoscopy

Subject undergoing upper endoscopy will have 2 biopsies performed, 1 each from the antrum and corpus. These will be collected, placed in transport media provided, and sent for culture and antibiotic sensitivity studies, as detailed within the laboratory manual. These will be used to aid in the determination of antibiotic resistance and possible effects on the efficacy of treatment with the test formulation. Antibiotic susceptibility testing will be conducted at the Baylor College of Medicine using agar dilution methodology Pharmacokinetic Evaluations Blood samples for the determination of baseline and trough plasma concentrations of amoxicillin, omeprazole, rifabutin, and 25-O-desacetyl-rifabutin are collected. Every effort should be made to ensure that the test formulation or placebo doses are administered 8 hours apart on the day before and on the day of PK sampling.

Time of blood sample collection is determined relative to the start of dose administration (i.e., time at start of administration of first capsule).

Plasma samples are analyzed using validated methodology. The minimum observed plasma concentration ($C_{min}$) of each analyte on Days 8 and 15 are determined by inspection and compared with baseline values ($C_0$).

Sample Size Determination

The effectiveness of any combination of two out of the three API components of test formulation is shown to be no more than 70%. The new regimen is expected to be at least 10% more effective than the standard of therapy using clarithromycin or metronidazole and amoxicillin and PPI The targeted effectiveness of the test formulation is equal to or higher than 90% (ITT: Intention to Treat).

The study design is based on the following specifications:
  The one-sided probability of a false positive outcome (i.e., concluding that the success probability is ≥90% when in fact it is only ≤70%) is 0.025,
  The power (i.e., the probability of concluding that the probability of success is ≥90% when it truly is 90%) is 0.9.

Using these specifications 42 patients are required to enroll in the active arm of the study.

Statistical Analyses
Primary Endpoint

The primary efficacy endpoint in this study is eradication of *H. pylori* among subjects randomized to active treatment, documented by $^{13}$C UBT test results at the test of cure visit (Visit 4). Subjects who are randomized to active treatment are evaluated for test of cure at Visit 4.

Subjects with negative test results are considered treatment successes. Subjects who test positive for *H. pylori* infection, those with indeterminate, not assessable, or missing results, or those not completing the test of cure visit are considered treatment failures. All efforts are made to obtain data from the test of cure visit for each subject receiving randomized treatment.

The statistical hypothesis that the active treatment is at least 70% effective will be tested against the alternative hypothesis that the active treatment is less than 70% effective using a one-sample Z-test. This hypothesis will be evaluated using the ITT population. Similar hypothesis testing is conducted using the per-protocol population, as a sensitivity analysis.

Secondary Endpoints

The secondary endpoints are as follows:
1. The occurrence and seriousness of adverse events are summarized by randomization group and treatment period, using the safety population.
2. The pharmacokinetic profiles of amoxicillin, omeprazole, rifabutin and the rifabutin metabolite 25-O-desacetyl-rifabutin are summarized over time.

A total of 90 patients are to be included in the study. All patients enrolled are to be H-*pylori* and fecal antigen test positive prior to enrollment. The study drug is to be administered for 14 days and post-treatment *H-pylori* status is to be assessed by UBT at least 4 weeks after treatment completion. Eradication is to be considered successful in the case of a negative UBT test. All patients are to be treated with the test formulation (rifabutin (150 mg daily), omperazole (120 mg daily) and amoxicillin (3 grams daily)) or placebo for 14 days. Drug tolerability, compliance and clinical laboratory tests were documented by the investigators during and after-treatment. The intention-to-treat eradication rates are targeted to be 70% or greater, 80% or greater, 84% or greater, 90% or greater. In some embodiments, intention-to-treat eradication rates are targeted to be between 70% and 80%, between 70% and 84%, 84% or greater, between 84% and 90%, 90% or greater. In some embodiments, treatment of patient for 14 days with the pharmaceutical composition is greater than 80%. In some embodiments, treatment of patient for 14 days with the pharmaceutical composition is greater than 84%. In some embodiments, treatment of patient for 14 days with the pharmaceutical composition is 90% or greater. In some embodiments, treatment of patient for 7 days with the pharmaceutical composition is 70% or greater. In some embodiments, treatment of patient for 7 days with the pharmaceutical composition is greater than 60%. In some embodiments, treatment of patient for 10 days with the pharmaceutical composition is greater than 70%. In some embodiments, treatment of patient for 10 days with the pharmaceutical composition is greater than 80%.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A kit comprising:
 a 14 day supply of capsules for eradicating *H. pylori* infection with an effectiveness greater than 80%, the 14 day supply including 168 all-in-one capsules filled with minitablets, wherein each capsule comprises 12.5 mg rifabutin/250 mg amoxicillin mixed minitablets and 10 mg omeprazole minitablets; and
 instructions to administer orally 4 capsules from the 14 day supply three times daily for a total daily oral dose of 150 mg rifabutin, 3000 mg amoxicillin, and 120 mg omeprazole for 14 days.

2. The kit of claim 1, wherein the 14 day supply of capsules is sufficiently designed to result in an eradication rate greater than 85%.

3. The kit of claim 1, wherein the 14 day supply of capsules is sufficiently designed to result in an eradication rate greater than 90%.

4. The kit of claim 1, wherein the 14 day supply of capsules is sufficiently designed to result in an eradication rate greater than 95%.

5. The kit of claim 1 wherein the amoxicillin is amoxicillin trihydrate.

6. The kit of claim 1 wherein the omeprazole is magnesium omeprazole.

* * * * *